US012410401B2

(12) United States Patent
Slukvin et al.

(10) Patent No.: US 12,410,401 B2
(45) Date of Patent: Sep. 9, 2025

(54) GENERATION OF FUNCTIONAL NEUTROPHILS AND MACROPHAGES FROM INDUCED PLURIPOTENT STEM CELLS IN CHEMICALLY DEFINED CONDITIONS USING TRANSIENT EXPRESSION OF ETV2

(71) Applicant: Wisconsin Alumni Research Foundation, Madison, WI (US)

(72) Inventors: Igor I. Slukvin, Verona, WI (US); Vera Sergeyevna Brok Volchanskaya, Singapore (SG); Kran Suknuntha, Madison, WI (US); Anna Huttenlocher, Madison, WI (US); David Alfred Bennin, Mount Horeb, WI (US); Lucas Klemm, Madison, WI (US)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 640 days.

(21) Appl. No.: 16/894,569

(22) Filed: Jun. 5, 2020

(65) Prior Publication Data

US 2020/0385676 A1    Dec. 10, 2020

Related U.S. Application Data

(60) Provisional application No. 62/858,173, filed on Jun. 6, 2019.

(51) Int. Cl.
| | | |
|---|---|---|
| *C12N 5/0783* | (2010.01) | |
| *A61K 40/10* | (2025.01) | |
| *A61K 40/42* | (2025.01) | |
| *A61K 40/45* | (2025.01) | |
| *C12N 5/0786* | (2010.01) | |

(52) U.S. Cl.
CPC ........... *C12N 5/0636* (2013.01); *A61K 40/10* (2025.01); *A61K 40/4242* (2025.01); *A61K 40/4544* (2025.01); *C12N 5/0645* (2013.01); *C12N 2500/02* (2013.01); *C12N 2501/113* (2013.01); *C12N 2501/155* (2013.01); *C12N 2501/165* (2013.01); *C12N 2501/23* (2013.01); *C12N 2501/26* (2013.01); *C12N 2501/599* (2013.01); *C12N 2506/45* (2013.01)

(58) Field of Classification Search
CPC ............. C12N 5/0636; C12N 2500/02; C12N 2501/113; C12N 2501/155; C12N 2501/165; C12N 2501/23; C12N 2501/26; C12N 2501/599; C12N 2501/115; C12N 2501/60; C12N 2510/00; A61K 40/10
See application file for complete search history.

(56) References Cited

U.S. PATENT DOCUMENTS

| | | |
|---|---|---|
| 5,652,122 A | 7/1997 | Frankel |
| 5,674,980 A | 10/1997 | Frankel |
| 6,841,535 B2 | 1/2005 | Divita |
| 6,881,825 B1 | 4/2005 | Robbins |
| 7,964,196 B2 | 6/2011 | De Los Rios |
| 8,546,140 B2 | 10/2013 | Mack |
| 8,846,395 B2 | 9/2014 | Slukvin |
| 9,382,531 B2 | 7/2016 | Slukvin |
| 2012/0046346 A1 | 2/2012 | Rossi |

FOREIGN PATENT DOCUMENTS

| | | | |
|---|---|---|---|
| WO | WO 2016/207256 A1 | * | 12/2016 |
| WO | WO 2017/079738 A1 | * | 5/2017 |

OTHER PUBLICATIONS

Fleming et al ("Endothelial cell-specific markers: going . . . going . . . gone;" Blood Aug. 1, 2005 vol. 106, No. 3 ) (Year: 2005).*
Choi et al ("Hematopoietic differentiation and production of mature myeloid cells from human pluripotent stem cells," Nature Protocols vol. 6 No. 3, 2011) (Year: 2011).*
Allouche et al ("The Role of Fibroblast Growth Factor-2 (FGF-2) in Hematopoiesis," Progress in Growth Factor Research, vol. 6. pp. 35-48, 1995) (Year: 1995).*
Mariani et al ("Mature CD101 and immature CD102 neutrophils present in G-CSF-treated donors display opposite effects on T cells," Blood, Mar. 9, 2017 vol. 129, No. 10) (Year: 2017).*
Ortmann et al ("Age is the work of art? Impact of neutrophil and organism age on neutrophil extracellular trap formation," Cell and Tissue Research (2018) 371:473-488). (Year: 2018).*
Orr et al ("Circulating CD10-/CD16 low neutrophils provide a quantitative index of active bone marrow neutrophil release," British Journal of Haematology,131, 508-519 2005) (Year: 2005).*
Yu, J., et al. (2009). Human induced pluripotent stem cells free of vector and transgene sequences. Science 324, 797-801.
Zarco, M.A. et al. Phenotypic changes in neutrophil granulocytes of healthy donors after G-CSF administration. Haematologica 84, 874-878 (1999).
Zhao, H. el al. A CRISPR screen identifies genes controlling Etv2 threshold expression in murine hemangiogenic fate commitment. Nat Commun 8, 541 (2017).
Yusa, K., et al. "A hyperactive piggyBac transposase for mammalian applications." Proceedings of the National Academy of Sciences 108.4 (2011): 1531-1536.
Ackermann M, et al. Bioreactor-based mass production of human iPSC-derived macrophages enables immunotherapies against bacterial airway infections. Nat Commun. 2018;9(1):5088.

(Continued)

*Primary Examiner* — Christopher M Babic
*Assistant Examiner* — Masudur Rahman
(74) *Attorney, Agent, or Firm* — McDonnell Boehnen Hulbert & Berghoff LLP

(57) ABSTRACT

The present invention provides methods of producing in vitro derived neutrophils or macrophages in xenogen- and serum-free conditions from pluripotent stem cells and in vitro derived populations of neutrophils and macrophages. Methods of treatment using in vitro derived neutrophils or macrophages are also contemplated.

6 Claims, 10 Drawing Sheets

Specification includes a Sequence Listing.

(56) References Cited

OTHER PUBLICATIONS

Altschul, S. F., et al. "Gapped BLAST and PSI-BLAST: a new generation of protein database search programs." Nucleic acids research 25.17 (1997): 3389-3402.
Badieyan, Z.S., et al. (2019). Concise Review: Application of Chemically Modified mRNA in Cell Fate Conversion and Tissue Engineering. Stem Cells Transl Med 8, 833-843.
Becker-Hapak, M. et al. "Protein Transduction: Generation of Full-Length Transducible Proteins Using the TAT System." Current protocols in cell biology 18.1 (2003): 20-2.
Blobel, G. A. et al. "Rescue of GATA-1-deficient embryonic stem cells by heterologous GATA-binding proteins." Molecular and Cellular Biology 15.2 (1995): 626-633.
Castagnola, E. et al. A prospective study on the epidemiology of febrile episodes during chemotherapy-induced neutropenia in children with cancer or after hemopoietic stem cell transplantation. Clin Infect Dis 45, 1296-1304 (2007).
Cavnar, P.J., et al. The actin regulatory protein HS1 interacts with Arp2/3 and mediates efficient neutrophil chemotaxis. J Biol Chem 287, 25466-25477 (2012).
Chen, G., et al. (2011). Chemically defined conditions for human iPSC derivation and culture. Nat Methods 8, 424-429.
Choi, K.D. et al. Hematopoietic and endothelial differentiation of human induced pluripotent stem cells. Stem Cells 27, 559-567 (2009).
Choi, K.D., et al. Generation of mature human myelomonocytic cells through expansion and differentiation of pluripotent stem cell-derived lin-CD34+CD43+CD45+ progenitors. J Clin Invest 119, 2818-2829 (2009).
Elcheva, I. et al. Direct induction of haematoendothelial programs in human pluripotent stem cells by transcriptional regulators. Nat Commun 5, 4372 (2014).
Fares, I. et al. Cord blood expansion. Pyrimidoindole derivatives are agonists of human hematopoietic stem cell self-renewal. Science 345, 1509-1512 (2014).
Garry, D.J. (2016). Etv2 Is a Master Regulator of Hematoendothelial Lineages. Trans Am Clin Climatol Assoc 127, 212-223.
Gea-Banacloche, J. (2017). Granulocyte transfusions: A concise review for practitioners. Cytotherapy 19, 1256-1269.
Gokcebay, DG et al. Granulocyte transfusions in the management of neutropenic fever: A pediatric perspective. Transfus Apher Sci 57, 16-19 (2018).
Graw, R.G., et al. Normal granulocyte transfusion therapy: treatment of septicemia due to gram-negative bacteria. N Engl J Med 287, 367-371 (1972).
Hayashi, M. et al. Endothelialization and altered hematopoiesis by persistent Etv2 expression in mice. Exp Hematol 40, 738-750 e711 (2012).
Henikoff, S. et al. "Amino acid substitution matrices from protein blocks." Proceedings of the National Academy of Sciences 89.22 (1992): 10915-10919.
Hu, K. et al. Efficient generation of transgene-free induced pluripotent stem cells from normal and neoplastic bone marrow and cord blood mononuclear cells. Blood 117, e109-119 (2011).
Kang, H. et al. GATA2 Is Dispensable for Specification of Hemogenic Endothelium but Promotes Endothelial-to-Hematopoietic Transition. Stem cell reports (2018).
Kataoka, H. et al. Etv2/ER71 induces vascular mesoderm from Flk1+PDGFRalpha+ primitive mesoderm. Blood 118, 6975-6986 (2011).
Klug, A. "The discovery of zinc fingers and their development for practical applications in gene regulation and genome manipulation." Quarterly reviews of biophysics 43.1 (2010): 1.
Kuijpers, T.W. et al. Membrane surface antigen expression on neutrophils: a reappraisal of the use of surface markers for neutrophil activation. Blood 78, 1105-1111 (1991).
Lachmann, N. et al. Large-scale hematopoietic differentiation of human induced pluripotent stem cells provides granulocytes or macrophages for cell replacement therapies. Stem cell reports 4, 282-296 (2015).
Li, L. et al. Am80-GCSF synergizes myeloid expansion and differentiation to generate functional neutrophils that reduce neutropenia-associated infection and mortality. EMBO Mol Med 8, 1340-1359 (2016).
Liao JK, et al. Rho kinase (ROCK) inhibitors. J Cardiovasc Pharmacol. 2007;50(1):17-24.
Lyman, G.H. et al. A Patient Risk Model of Chemotherapy-Induced Febrile Neutropenia: Lessons Learned From the ANC Study Group. J Natl Compr Canc Netw 15, 1543-1550 (2017).
Mesquitta, W.T., et al.(2019). UM171 expands distinct types of myeloid and NK progenitors from human pluripotent stem cells. Sci Rep 9, 6622.
Needleman, S.B. et al. "A general method applicable to the search for similarities in the amino acid sequence of two proteins." Journal of molecular biology 48.3 (1970): 443-453.
Pearson, W. R. "Rapid and sensitive sequence comparison with FASTP and FASTA." Methods in enzymology 183 (1990): 63-98.
Pearson, W. R., et al. (1988). Improved tools for biological sequence comparison. Proceedings of the National Academy of Sciences, 85(8), 2444-2448.
Penchansky, L., et al. Flow cytometric study of the expression of neutral endopeptidase (CD10/CALLA) on the surface of newborn granulocytes. Mod Pathol 6, 414-418 (1993).
Piechaczek, C., et al. "A vector based on the SV40 origin of replication and chromosomal S/MARs replicates episomally in CHO cells." Nucleic acids research 27.2 (1999): 426-428.
Powell, D. et al. Chemokine Signaling and the Regulation of Bidirectional Leukocyte Migration in Interstitial Tissues. Cell Rep 19, 1572-1585 (2017).
Saeki, K. et al. A feeder-free and efficient production of functional neutrophils from human embryonic stem cells. Stem Cells 27, 59-67 (2009).
Scapini, P., et al. Human neutrophils in the saga of cellular heterogeneity: insights and open questions. Immunol Rev 273, 48-60 (2016).
Sellers, P. H. "On the theory and computation of evolutionary distances." SIAM Journal on Applied Mathematics 26.4 (1974): 787-793.
Slukvin, I.I., et al. Directed differentiation of human embryonic stem cells into functional dendritic cells through the myeloid pathway. Journal of Immunology 176, 2924-2932 (2006).
Suknuntha, K. et al. Optimization of Synthetic mRNA for Highly Efficient Translation and its Application in the Generation of Endothelial and Hematopoietic Cells from Human and Primate Pluripotent Stem Cells. Stem Cell Rev 14, 525-534 (2018).
Sumanas, S. et al. ETS Transcription Factor ETV2/ER71/Etsrp in Hematopoietic and Vascular Development. Curr Top Dev Biol 118, 77-111 (2016).
Sweeney, C.L. et al. Molecular Analysis of Neutrophil Differentiation from Human Induced Pluripotent Stem Cells Delineates the Kinetics of Key Regulators of Hematopoiesis. Stem Cells 34, 1513-1526 (2016).
Trump, L.R. et al. Neutrophils Derived from Genetically Modified Human Induced Pluripotent Stem Cells Circulate and Phagocytose Bacteria In Vivo. Stem Cells Transl Med (2019).
U.S. Pharmacopeia National Formulary, 1857-1859, (1990).
Valentini, C.G., et al. Granulocyte Transfusions: A Critical Reappraisal. Biol Blood Marrow Transplant 23, 2034-2041 (2017).
Warrick, J.W., et al. Tools for Single-Cell Kinetic Analysis of Virus-Host Interactions. PLoS One 11, e0145081 (2016).
Werfel, T., et al. Rapid increases in the membrane expression of neutral endopeptidase (CD10), aminopeptidase N (CD13), tyrosine phosphatase (CD45), and Fc gamma-RIII (CD16) upon stimulation of human peripheral leukocytes with human C5a. J Immunol 147, 3909-3914 (1991).
West, K.A., et al. Granulocyte transfusions in the management of invasive fungal infections. Br J Haematol 177, 357-374 (2017).

(56) References Cited

OTHER PUBLICATIONS

Wilson, K. A., et al. (2013). Design and development of artificial zinc finger transcription factors and zinc finger nucleases to the hTERT locus. Molecular Therapy-Nucleic Acids, 2, e87.

Yamahashi, Y. et al. Integrin associated proteins differentially regulate neutrophil polarity and directed migration in 2D and 3D. Biomed Microdevices 17, 100 (2015).

Yates, J., et al. (1984). A cis-acting element from the Epstein-Barr viral genome that permits stable replication of recombinant plasmids in latently infected cells. Proceedings of the National Academy of Sciences, 81(12), 3806-3810.

* cited by examiner

SEQUENCE LISTING

```
<160> NUMBER OF SEQ ID NOS: 10

<210> SEQ ID NO 1
<211> LENGTH: 342
<212> TYPE: PRT
<213> ORGANISM: Homo sapiens

<400> SEQUENCE: 1

Met Asp Leu Trp Asn Trp Asp Glu Ala Ser Pro Gln Glu Val Pro Pro
1               5                   10                  15

Gly Asn Lys Leu Ala Gly Leu Glu Gly Ala Lys Leu Gly Phe Cys Phe
            20                  25                  30

Pro Asp Leu Ala Leu Gln Gly Asp Thr Pro Thr Ala Thr Ala Glu Thr
        35                  40                  45

Cys Trp Lys Gly Thr Ser Ser Leu Ala Ser Phe Pro Gln Leu Asp
    50                  55                  60

Trp Gly Ser Ala Leu Leu His Pro Glu Val Pro Trp Gly Ala Glu Pro
65                  70                  75                  80

Asp Ser Gln Ala Leu Pro Trp Ser Gly Asp Trp Thr Asp Met Ala Cys
                85                  90                  95

Thr Ala Trp Asp Ser Trp Ser Gly Ala Ser Gln Thr Leu Gly Pro Ala
            100                 105                 110

Pro Leu Gly Pro Gly Pro Ile Pro Ala Ala Gly Ser Glu Gly Ala Ala
        115                 120                 125

Gly Gln Asn Cys Val Pro Val Ala Gly Glu Ala Thr Ser Trp Ser Arg
    130                 135                 140

Ala Gln Ala Ala Gly Ser Asn Thr Ser Trp Asp Cys Ser Val Gly Pro
145                 150                 155                 160

Asp Gly Asp Thr Tyr Trp Gly Ser Gly Leu Gly Gly Glu Pro Arg Thr
                165                 170                 175

Asp Cys Thr Ile Ser Trp Gly Gly Pro Ala Gly Pro Asp Cys Thr Thr
            180                 185                 190

Ser Trp Asn Pro Gly Leu His Ala Gly Gly Thr Thr Ser Leu Lys Arg
        195                 200                 205

Tyr Gln Ser Ser Ala Leu Thr Val Cys Ser Glu Pro Ser Pro Gln Ser
    210                 215                 220

Asp Arg Ala Ser Leu Ala Arg Cys Pro Lys Thr Asn His Arg Gly Pro
225                 230                 235                 240

Ile Gln Leu Trp Gln Phe Leu Leu Glu Leu Leu His Asp Gly Ala Arg
                245                 250                 255

Ser Ser Cys Ile Arg Trp Thr Gly Asn Ser Arg Glu Phe Gln Leu Cys
```

```
                260                 265                 270
Asp Pro Lys Glu Val Ala Arg Leu Trp Gly Glu Arg Lys Arg Lys Pro
            275                 280                 285
Gly Met Asn Tyr Glu Lys Leu Ser Arg Gly Leu Arg Tyr Tyr Tyr Arg
        290                 295                 300
Arg Asp Ile Val Arg Lys Ser Gly Gly Arg Lys Tyr Thr Tyr Arg Phe
305                 310                 315                 320
Gly Gly Arg Val Pro Ser Leu Ala Tyr Pro Asp Cys Ala Gly Gly
            325                 330                 335
Arg Gly Ala Glu Thr Gln
            340

<210> SEQ ID NO 2
<211> LENGTH: 148
<212> TYPE: PRT
<213> ORGANISM: Homo sapiens

<400> SEQUENCE: 2

Thr Lys Thr Leu Met Lys Lys Asp Lys Tyr Thr Leu Pro Gly Gly Leu
1               5                   10                  15
Leu Ala Pro Gly Gly Asn Ser Met Ala Ser Gly Val Gly Val Gly Ala
            20                  25                  30
Gly Leu Gly Ala Gly Val Asn Gln Arg Met Asp Ser Tyr Ala His Met
        35                  40                  45
Asn Gly Trp Ser Asn Gly Ser Tyr Ser Met Met Gln Asp Gln Leu Gly
    50                  55                  60
Tyr Pro Gln His Ser Thr Thr Ala Pro Ile Thr Asp Val Ser Leu Gly
65                  70                  75                  80
Asp Glu Leu Arg Leu Asp Gly Glu Glu Val Asp Met Thr Pro Ala Asp
            85                  90                  95
Ala Leu Asp Asp Phe Asp Leu Glu Met Leu Gly Asp Val Glu Ser Pro
        100                 105                 110
Ser Pro Gly Met Thr His Asp Pro Val Ser Tyr Gly Ala Leu Asp Val
        115                 120                 125
Asp Asp Phe Glu Phe Glu Gln Met Phe Thr Asp Ala Leu Gly Ile Asp
        130                 135                 140
Asp Phe Gly Gly
145

<210> SEQ ID NO 3
<211> LENGTH: 81
<212> TYPE: PRT
<213> ORGANISM: Homo sapiens

<400> SEQUENCE: 3

Pro Ile Gln Leu Trp Gln Phe Leu Leu Glu Leu Leu His Asp Gly Ala
1               5                   10                  15
Arg Ser Ser Cys Ile Arg Trp Thr Gly Asn Ser Arg Glu Phe Gln Leu
            20                  25                  30
Cys Asp Pro Lys Glu Val Ala Arg Leu Trp Gly Glu Arg Lys Arg Lys
        35                  40                  45
Pro Gly Met Asn Tyr Glu Lys Leu Ser Arg Gly Leu Arg Tyr Tyr Tyr
    50                  55                  60
Arg Arg Asp Ile Val Arg Lys Ser Gly Gly Arg Lys Tyr Thr Tyr Arg
65                  70                  75                  80
Phe
```

```
<210> SEQ ID NO 4
<211> LENGTH: 1490
<212> TYPE: DNA
<213> ORGANISM: Homo sapiens

<400> SEQUENCE: 4
gcagataagc ccagcttagc ccagctgacc ccagaccctc tccctcact ccccccatgt      60
cgcaggatcg agaccctgag gcagacagcc cgttcaccaa gcccccgcc ccgcccat       120
caccccgtaa acttctccca gcctccgccc tgccctcacc cagcccgctg ttccccaagc    180
ctcgctccaa gcccacgcca ccctgcagc agggcagccc cagaggccag cacctatccc     240
cgaggctggg gtcgaggctc ggccccgccc ctgcctctgc aacttgagcc tggctgcgac    300
ccctgctctg acgtctcgga aaattcccc ttgcccaggc ccttggggga gggggtgcat     360
ggtatgaaat ggggctgaga ccccggctg ggggcagagg aacccgccag agaacattca     420
gaaggccttc atcgcatcca tggacctgtg gaactgggat gaggcatccc cacaggaagt    480
gcctccaggg aacaagctgg cagggcttga aggagccaaa ttaggcttct gtttccctga    540
tctggcactc caaggggaca cgccgacagc gacagcagag acatgctgga aaggtacaag    600
ctcatccctg gcaagcttcc cacagctgga ctggggctcc gcgttactgc acccagaagt    660
tccatgggg gcggagcccg actctcaggc tcttccgtgg tccggggact ggacagacat     720
ggcgtgcaca gcctgggact cttggagcgg cgcctcgcag accctgggcc ccgcccctct    780
cggcccgggc cccatccccg ccgccggctc cgaaggcgcc gcgggccaga actgcgtccc    840
cgtggcggga gaggccacct cgtggtcgcg cgcccaggcc gccgggagca acaccagctg    900
ggactgttct gtggggcccg acggcgatac ctactgggc agtggcctgg cggggagcc     960
gcgcacggac tgtaccattt cgtggggcgg gcccgcgggc ccggactgta ccacctcctg   1020
gaacccgggg ctgcatgcgg gtggcaccac ctctttgaag cggtaccaga gctcagctct   1080
caccgtttgc tccgaaccga gcccgcagtc ggaccgtgcc agtttggctc gatgcccaa    1140
aactaaccac cgaggtccca ttcagctgtg gcagttcctc ctggagctgc tccacgacgg   1200
ggcgcgtagc agctgcatcc gttggactgg caacagccgc gagttccagc tgtgcgaccc   1260
caaagaggtg gctcggctgt ggggcgagcg caagagaaag ccgggcatga attacgagaa   1320
gctgagccgg ggccttcgct actactatcg ccgcgacatc gtgcgcaaga gcggggggcg   1380
aaagtacacg taccgcttcg ggggccgcgt gcccagccta gcctatccgg actgtgcggg   1440
aggcggacgg ggagcagaga cacaataaaa attcccggtc aaacctcaaa              1490

<210> SEQ ID NO 5
<211> LENGTH: 11
<212> TYPE: PRT
<213> ORGANISM: Artificial Sequence
<220> FEATURE:
<223> OTHER INFORMATION: synthetic

<400> SEQUENCE: 5

Tyr Gly Arg Lys Lys Arg Arg Gln Arg Arg Arg
1               5                   10

<210> SEQ ID NO 6
<211> LENGTH: 8
<212> TYPE: PRT
<213> ORGANISM: Artificial Sequence
<220> FEATURE:
<223> OTHER INFORMATION: synthetic
```

```
<400> SEQUENCE: 6

Arg Lys Lys Arg Arg Gln Arg Arg
1               5

<210> SEQ ID NO 7
<211> LENGTH: 11
<212> TYPE: PRT
<213> ORGANISM: Artificial Sequence
<220> FEATURE:
<223> OTHER INFORMATION: synthetic

<400> SEQUENCE: 7

Tyr Ala Arg Ala Ala Ala Arg Gln Ala Arg Ala
1               5                   10

<210> SEQ ID NO 8
<211> LENGTH: 11
<212> TYPE: PRT
<213> ORGANISM: Artificial Sequence
<220> FEATURE:
<223> OTHER INFORMATION: synthetic

<400> SEQUENCE: 8

Thr His Arg Leu Pro Arg Arg Arg Arg Arg
1               5                   10

<210> SEQ ID NO 9
<211> LENGTH: 11
<212> TYPE: PRT
<213> ORGANISM: Artificial Sequence
<220> FEATURE:
<223> OTHER INFORMATION: synthetic

<400> SEQUENCE: 9

Gly Gly Arg Arg Ala Arg Arg Arg Arg Arg
1               5                   10

<210> SEQ ID NO 10
<211> LENGTH: 22
<212> TYPE: DNA
<213> ORGANISM: Artificial Sequence
<220> FEATURE:
<223> OTHER INFORMATION: synthetic - primer

<400> SEQUENCE: 10
atcggtgcgg gcctcttcgc ta                                              22
```

GENERATION OF FUNCTIONAL NEUTROPHILS AND MACROPHAGES FROM INDUCED PLURIPOTENT STEM CELLS IN CHEMICALLY DEFINED CONDITIONS USING TRANSIENT EXPRESSION OF ETV2

CROSS-REFERENCE TO RELATED APPLICATIONS

This application claims priority to U.S. Provisional Application No. 62/858,173 filed on Jun. 6, 2019, the contents of which are incorporated by reference in its entirety.

STATEMENT REGARDING FEDERALLY SPONSORED RESEARCH

This invention was made with government support under OD011106, HL142665 and AI134749 awarded by the National Institutes of Health. The government has certain rights in the invention.

SEQUENCE LISTING

A Sequence Listing accompanies this application and is submitted as an ASCII text file of the sequence listing named "960296_04043_ST25.txt" which is 8.60 kb in size and was created on Jun. 5, 2020. The sequence listing is electronically submitted via EFS-Web with the application and is incorporated herein by reference in its entirety.

BACKGROUND OF THE INVENTION

The field of the invention is related to methods of obtaining neutrophils from pluripotent stem cells and methods of use.

Despite recent advances in prevention and management, myelosuppression and febrile neutropenia remains one of the most disturbing complications of cancer therapies and common cause of morbidity and mortality especially in pediatric cancer patients[1, 2]. In pioneering studies, correcting neutropenia with granulocyte transfusion was shown to be efficient in the clinical management of septicemia[3]. Although recent clinical trials produced inconclusive evidence concerning its efficiency, granulocyte transfusion is still perceived as a life-saving support in neutropenic patients, especially in pediatric patients resistant to antimicrobial therapies[4-7]. However, the complicated logistics of granulocyte collection, the need for pre-treating donors with G-CSF or steroids, difficulties in collecting a sufficient number of good quality granulocytes and the limited storage time (24 hours); all hampers the utility of granulocyte transfusion for correcting neutropenia, and may contribute to the inconclusive results observed in clinical trials.

Macrophages are central effectors in the innate immunity which detect and eliminate bacterial and cancer cells. Applying macrophages to enhance immunity and clear infected and malignant cells is a promising strategy for novel cell-based therapies.

Human induced pluripotent stem cells (hiPSCs) offer the potential to serve as a versatile and scalable source of granulocytes and macrophages, which could be coupled with genetic engineering technologies to meet specific clinical needs. Although our group and others have demonstrated feasibility of neutrophil and macrophage generation from hiPSCs[8-12], previously described methods rely on the use of serum, feeder[35] or embryoid body formation, which hampers their adoption for GMP manufacturing and clinical use.

There is a need for efficient in vitro production of neutrophils from PSCs in serum- and feeder-free conditions that is scalable for GMP manufacturing and to produce clinically useable cells.

There is also a need for the ability to provide genetically modifiable neutrophils which provides unique properties from naturally derived neutrophils providing the ability to manipulate from human treatment.

SUMMARY OF THE INVENTION

The present invention provides in vitro methods of differentiating, and/or expanding neutrophils from pluripotent stem cells and methods of use.

The present disclosure provides methods of differentiating and/or expanding PSCs into neutrophils under serum-free and feeder-free conditions.

A three step protocol for efficient neutrophil production from hiPSCs in 2D serum- and feeder-free conditions was developed using direct programming with modified mRNA (mmRNA). Initially, hiPSCs are directly programmed into hematoendothelial progenitors using ETV2 mmRNA which then differentiated into myeloid progenitors in the presence of GM-CSF, FGF2 and UM171. Non-adherent myeloid progenitors can be continuously collected from cultures every 8-10 days for up to 30 days post ETV2 transfection, and subsequently differentiated into mature neutrophils in the presence of G-CSF and a retinoic acid agonist, for example, Am580. This method significantly expedites generation of neutrophils with the first batch of neutrophils available as soon as 14 days after initiation of differentiation and allows the generation of up to $1.7 \times 10^7$ neutrophils from $10^6$ hPSCs. Further, these in vitro derived neutrophils are genetically manipulatable, which is not true for donor derived neutrophils, and therefore can be genetically altered relative to conditions needed for the specific treatments.

The proposed differentiation system may be suitable for generating mature functional granulocytic cells for correction of neutropenia and gene therapies.

In one aspect, the disclosure provides an in vitro method of producing $CD16^+CD10^-$ neutrophils from pluripotent stem cells (PSCs) in serum-free medium, the method comprising: (a) transiently introducing exogenous ETV2 in the PSCs and culturing the ETV2-induced PSCs in xenogen-free serum-free medium comprising FGF-2 to produce a population of ETV2-induced $CD144^+$ hematoendothelial progenitor cells (ETV2-induced HEPs); (b) culturing the ETV2-induced $CD144^+$ thematoendothelial progenitor cells in xenogen-free serum-free medium comprising GM-CSF and FGF2 for a sufficient time to produce non-adherent myeloid progenitors; and (c) culturing the non-adherent myeloid progenitors in xenogen-free serum-free medium comprising G-CSF and retinoic acid agonist to differentiate the myeloid progenitors into neutrophils.

In another aspect, the disclosure provides a population of neutrophils produced by the methods described herein.

In another aspect, the present disclosure provides a method of producing neutrophils, the method comprising: (a) culturing $CD144^+$ hematoendothelial progenitor cells derived from PSCs in xenogen-free serum-free medium comprising GM-CSF and FGF2 for a sufficient time to produce myeloid progenitors; and (b) culturing the myeloid progenitors in xenogen-free serum-free medium comprising G-CSF and retinoic acid agonist to differentiate the myeloid progenitors into neutrophils.

In another aspect, the disclosure provides a method of treating neutropenia in a subject, the method comprising administering an effective amount of the neutrophils made by the methods described herein to treat the neutropenia.

In yet another aspect, the disclosure provides a method of treating a burn or wound in a subject in need thereof, the method comprising administering an effective amount of the neutrophils made by the methods described herein to treat the burn or wound.

In another aspect, the disclosure provides a method of treating an infection in a subject in need thereof, the method comprising administering an effective amount of the neutrophils made by the methods described herein to treat the infection.

In yet another aspect, the disclosure provides an in vitro method of producing $CD14^+CD16^+$ macrophages from pluripotent stem cells (PSCs), the method comprising: (a) transiently introducing exogenous ETV2 into pluripotent stem cells and culturing the ETV2-induced PSCs in xenogen- and serum-free medium comprising FGF2 to produce ETV2-induced $CD144^+$hematoendothelial progenitor cells; (b) culturing the ETV2-induced $CD144^+$hematoendothelial progenitor cells in xenogen- and serum-free medium comprising GM-CSF and FGF-2 for about 4 days; and (c) culturing the cells of step (b) in medium comprising IL-3 and M-CSF to produce the $CD14^{3O}$ $CD16^+$ macrophages expressing CD68, CD80 and CD163.

In yet a further aspect, the disclosure provides an in vitro derived $CD14^+CD16^+$ macrophage population made by the methods described herein, wherein the macrophages further express CD68, CD80 and CD163.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

DETAILED DESCRIPTION OF THE INVENTION

Figure 1:
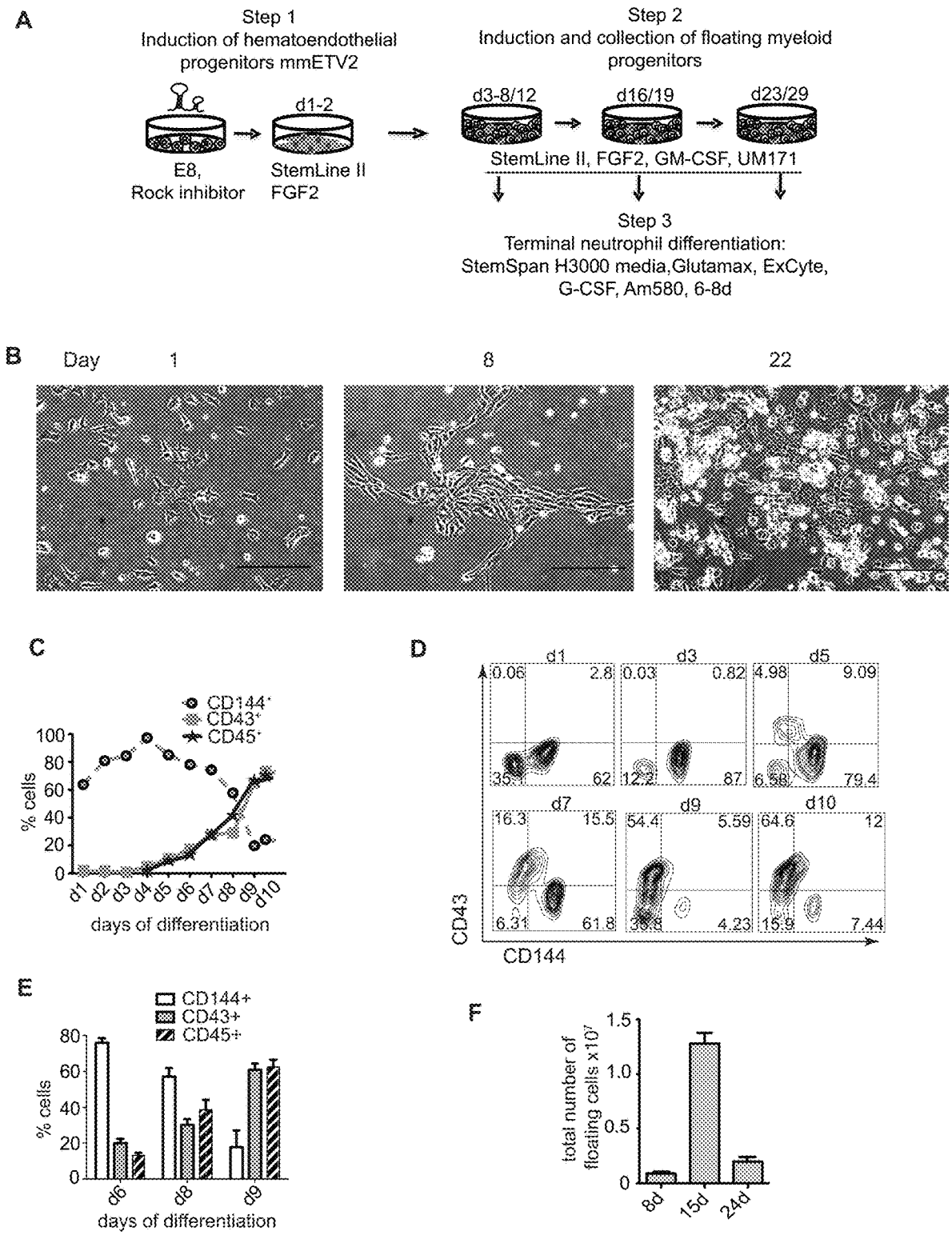
FIG. 1. Induction of hematoendothelial program following transduction hiPSCs with ETV2 mmRNA. (A) Schematic diagram of optimized protocol used for generation of neutrophils from hiPSCs in serum-, xeno- and feeder-free conditions. (B) Representative light microscopy images showing hematoendothelial development following transfection IISH2i-BM9 hiPSCs with ETV2 mmRNA and culture with FGF2 and GM-CSF. Scale bar is 300 μm. (C) and (D) Representative experiment showing kinetics of CD144 and CD43 expression in cultures. (E) Expression of CD144, CD43, and CD45 on day 6, 8 and 9 post-ETV2 transfection. Bars show mean±SE for 3 independent experiments. (F) Yield of floating myeloid cells in step 2 cultures from $10^6$ undifferentiated hiPSCs. Bars show mean±SE for 2 independent experiments.

The present disclosure describes methods of producing neutrophils from human induced pluripotent stem cells (hiPSCs) which can be scalable for use in producing therapeutic cells for therapeutic use. The disclosure describes a rapid, efficient, serum-, feeder- and xenogen-free protocol for neutrophil generation from hiPSCs. The method further allows for the production of genetically altered/modified neutrophils. The method is based on direct hematoendothelial programming of hiPSCs by transient expression of ETV2 within the cells (e.g., using ETV2 modified mRNA (mmRNA) which is less immunogenic and more stable form of mRNA). Culture of ETV2-induced hematoendothelial progenitors in the presence of GM-CSF, FGF2 and optionally UM171 led to continuous production of generous amounts of non-adherent CD34+CD4S+ myeloid progenitors which can be harvested every 8-10 days for up to 30 days of culture. Subsequently, the non-adherent myeloid progenitors can be differentiated into neutrophils in the presence of G-CSF and a retinoic acid agonist (e.g., Am580). In vitro derived neutrophils obtained under these serum-free and xenogen-free conditions displayed a typical somatic neutrophil morphology, produced reactive oxygen species, and possessed phagocytic and chemotactic activities. However, these neutrophils do not express CD10 and are impaired in their production of neutrophil extracellular traps (NETs) providing them with altered characteristics from naturally derived neutrophils that provides beneficial qualities for the cells to be used therapeutically. These in vitro derived cells can be used for a number of different therapeutic uses as described herein.

In addition, the disclosure also provides methods of producing $CD14^+CD16^+$ macrophages. Culturing of ETV2 modified mRNA transduced cells with GM-CSF and FGF2 with or without UM171 followed by isolation of the adherent cells and culture with IL-3 and M-CSF produce a population of macrophages, described in more detail herein.

The methods described generate a significant number of neutrophils and macrophages in GMP-compatible conditions (xenogen-free, feeder-cell free, serum-free conditions) for cell-therapy and gene-therapy applications. The described methods provide advances and advantages over previously described methods which relied on the use of serum in the medium, feeder cells or embryoid body formation, which hampers their adoption for GMP manufacturing and clinical use. Further, the ability to genetically modify the cells prior to differentiation allows for versatility of the use of the cells for therapeutic treatment.

In Vitro Methods of Producing Neutrophils

The present disclosure provides a three step protocol for efficient neutrophil production from pluripotent stem cells, particularly hiPSCs, in 2D system under serum- and feeder-free conditions using direct programming with transient expression of ETV2, e.g., by addition of modified mRNA (mmRNA) of ETV2 into the hiPSCs. Initially, in step 1, hiPSCs are directly programmed into hematoendothelial progenitors using ETV2 mmRNA which transiently produced ETV2 within the cells. In step 2, the hematoendothelial progenitors are then differentiated into myeloid progenitors in the presence of GM-CSF, FGF2 and optionally UM171 (the presence of UM171 in combination with GM-CSF and FGF2 increases the number of neutrophils produced by the methods). Myeloid progenitors which are non-adherent could be continuously collected from cultures every 8-10 days for up to 30 days of post ETV2 transfection. In step 3, these myeloid progenitors are subsequently differentiated into mature neutrophils in the presence of G-CSF and a retinoic acid agonist, preferably Am580. This method significantly expedites generation of neutrophils with the first batch of neutrophils available as soon as 14 days after initiation of differentiation and allows the generation of up to $1.7 \times 10^7$ neutrophils from $10^6$ hPSCs. The produced in vitro derived neutrophil cells are suitable for generating mature functional granulocytic cells for correction of neutropenia and gene therapies.

In one embodiment, an in vitro method of producing neutrophils from pluripotent stem cells (PSCs) is provided. The method comprises (a) transiently introducing exogenous ETV2 in the PSCs and culturing the ETV2-induced PSCs in xenogen-free medium comprising FGF-2 to produce a population of ETV2-induced $CD144^+$hematoendothelial progenitor cells (ETV2-induced HEPs); (b) culturing the ETV2-induced $CD144^+$hematoendothelial progenitor cells in xenogen-free medium comprising GM-CSF and FGF2 for a sufficient time to produce non-adherent myeloid progenitors (e.g., $CD34^+CD45^+$myeloid progenitors); and (c) culturing the myeloid progenitors in xenogen-free medium comprising G-CSF and retinoic acid agonist to differentiate the myeloid progenitors into CD16+CD10– neutrophils.

The first step, as shown in FIG. 1A, of the method comprises transiently introducing exogenous ETV2 in the PSCs and culturing in the presence of FGF-2 for a sufficient time to produce $CD144^+$hematoendothelial progenitor cells. In some aspects, the ETV2-induced PSCs are plated on coated plates (e.g., collagen coated plates) for culturing to produce the $CD144^+$thematoendothelial progenitor cells.

ETV2 can be transiently introduced into the PSCs by methods known in the art. It is important that the ETV-2 is only transiently expressed within the PSCs and ETV2-induced $CD144^+$hematoendothelial progenitor cells. Methods of transiently expressing ETV2 in PSCs are known in the art, and include, but are not limited to, for example, introducing transiently exogenous nucleic acids encoding the protein of interest (e.g., by plasmid expression vector transfection, or modified mRNA transfection); protein transduction, among others. In one embodiment, mmRNA of ETV-2 (e.g., Accession No: NM_014209.2; SEQ ID NO:4) is introduced into the PSCs by suitable methods. Methods of transiently expressing ETV2 in PSCs are described in U.S. Pat. No. 9,382,531, the contents of which are incorporated by reference in its entirety. Methods of introducing mmRNA into PSCs are known in the art, and include, but are not limited to, the method described in the Examples, for example, by transfection or electroporation. The methods of introducing mmRNA or DNA to transiently express ETV-2 protein is within the skill of one in the art and are not limited to what is demonstrated in the examples The term "introducing ETV2 . . . " encompasses the transient expression of ETV2 (SEQ ID NO:1), a protein comprising the ETV2 DNA binding domains (DBDs, SEQ ID NO:3) and a heterologous transactivation domain (TDs) or a homolog thereof that have the same functionality of ETV2. The skilled artisan recognizes that in many cases it is possible to substitute a native transactivation domain with an unrelated transactivation domain (e.g., VP16, GAL4, or LEX TDs) well known in the art and often used to generate functional heterologous transcription factors having a desired DBD, e.g., the ETV2 DBD (SEQ ID NO:3), and a heterologous TD, e.g. GATA1 (DBD)-VP16, as exemplified in Blobel et al (1995), Mol Cell Biol, 15(2):626-633. The amino acid sequence of the VP16 transactivation domain (SEQ ID NO:2). The present methods contemplate the ability to use any function homologs of ETV2 in the practice of the methods. A functional homolog may comprise the amino acid sequence of an artificial transcription factor that has no significant sequence identity to ETV2 (SEQ ID NO:1), but is able to bind and transactivate a cognate promoter sequence. For example, the artificial DBD may be generated by designing zinc finger-containing proteins having binding specificity for a designed target sequence (e.g., an ETV2 motif). The zinc-finger DBD is then fused to a transactivator protein, e.g., VP16 to generate a fusion protein that is an artificial TF. See, e.g., Wilson et al (2013), Mol Ther Nucleic Acids, (published online): 2, e87; doi:10.1038; and Klug (2010), Q Rev Biophys.; February; 43(1):1-21. doi: 10.1017/50033583510000089.

The present methods also contemplate using ETV proteins or a sequence with at least 75% identity to ETV2 (SEQ ID NO:1), preferably at least 80% identity to ETV2 (SEQ ID NO:1), more preferably at least 90% identity to ETV2 (SEQ ID NO:1), preferably at least 95% % identity to ETV2 (SEQ ID NO:1), alternatively at least 98% identity to SEQ ID NO:1, alternatively 99% sequence identity to SEQ ID NO:1, alternatively 100% sequence identity to SEQ ID NO:1.

Sequence identity between two or more amino acid sequences is determined by conventional methods. See, for example, Altschul et al., (1997), Nucleic Acids Research, 25(17):3389-3402; and Henikoff and Henikoff (1982), Proc. Natl. Acad. Sci. USA, 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the shorter sequence plus the number of gaps introduced into the longer sequence in order to align the two sequences]). Those skilled in the art will appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of another peptide. The FASTA algorithm is described by Pearson and Lipman (1988), Proc. Nat'l Acad. Sci. USA, 85:2444, and by Pearson (1990), Meth. Enzymol., 183:63. Briefly, FASTA first characterizes sequence similarity by identifying regions shared by the query sequence (e.g., any of SEQ ID NOs:1-7) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch (1970), J. Mol. Biol., 48:444-453; Sellers (1974), SIAM J. Appl. Math., 26:787), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson (1990), Meth. Enzymol., 183:63.

After initiating transient expression of ETV2 in the hPSCs, these cells are cultured for a period of about 24 hours to about 4 days in a serum-free xenogen-free medium suitable for culture of hPSCs. Serum-free, xenogen-free, medium suitable for culturing hPSCs are known in the art and include, but are not limited to, for example, StemLine II (commercially available from Sigma Aldrich), in the presence of FGF-2 (suitably, for example, about 10 ng/ml to about 50 ng/ml of FGF2). In some embodiments, the transient expression culture period is for at least two to about seven days, preferably in some embodiments, the transient ETV2 expression culture period is for about two to about four days. The hPSCs can be cultured on coated plates, for example, on collagen coated plates.

In some embodiments, transient expression of ETV2 in hPSCs is achieved by any of a number of established methods to introduce a mammalian expression vector, e.g., lipofection, electroporation, or nucleofection, into the cell. In some embodiments, mammalian expression vectors to be used are double-stranded nucleic acid vectors (e.g., episomal plasmid vectors, transposon vectors, or minicircle vectors). Mammalian expression vectors suitable for the methods described herein comprise a promoter competent to drive transient ETV2 expression in hPSCs and encode for the ETV2 protein. Suitable vectors are known in the art.

In some embodiments, transient expression of an ETV2 (SEQ ID NO:1) is carried out by double stranded DNA expression vectors ("DNA expression vectors") tbhe encode the ETV2. In some embodiments, the DNA expression vectors used in the reprogramming methods described herein also include loxP transposition target sites for CRE recombinase, which allows for subsequent excision of the vector. In other embodiments DNA expression vectors are episomal vectors that are stably maintained and replicate within host mammalian cells without genomic integration. Episomal vectors include a mammalian origin of replication, e.g., the Epstein-Barr Virus oriP element (Yates et al (1984), Proc. Natl. Acad. Sci. USA, 81:3806-3810, which allows episomal replication of the DNA expression vector in the hPSCs. Examples of vectors comprising a mammalian origin of replication are described in, e.g., U.S. Pat. No. 8,546,140. Episomal DNA expression vectors suitable for the methods described herein include, but are not limited to, any of the following episomal vectors: pCEP4, pREP4, or pEBNA DEST. In some embodiments, the DNA expression vectors suitable for the methods described herein include a S/MAR (scaffold/matrix attachment region) sequence. See, e.g., Piechaczek et al (1999), Nucleic Acids Res, 27:426-428, incorporated by reference in its entirety.

In a suitable embodiment, conditional expression of the ETV2 protein is contemplated to be used in the methods described herein. Suitable conditional expression systems are known in the art, including, but not limited to, for example, DOX-inducible system, tetracycline inducible expression system (Tet-On) and other systems known in the art.

In some embodiments, the mammalian expression vectors to be used are piggyBac transposon expression vectors, which are efficiently integrated into the genome of mammalian cells when transfected into the mammalian cells in the presence of a piggyBac transposase. Subsequently, a piggyback transposon can be excised from the genome of recombinant host cells, by transiently expressing a piggyback transposase. See, e.g., Yusa et al (2011), Proc. Natl Acad. Sci USA, 108:1531-1536.

In some embodiments transient expression of ETV2 is achieved by introduction of modified mRNAs (mmRNAs) encoding ETV2 into hPSCs, e.g., by transfection or electroporation. mmRNAs and their synthesis is described in detail in, e.g., U.S. Patent Application Publication No 20120046346. Typically, mmRNAs comprise (i) a 5' synthetic cap for enhanced translation; (ii) modified nucleotides that confer RNAse resistance and an attenuated cellular interferon response, which would otherwise greatly reduce translational efficiency; and (iii) a 3' poly-A tail. Typically, ETV2 mmRNAs are synthesized in vitro from a DNA template comprising an SP6 or T7 RNA polymerase promoter-operably linked to an open reading frame encoding an ETV2. The mmRNA synthesis reaction is carried in the presence of a mixture of modified and unmodified nucleotides. In some embodiments modified nucleotides included in the in vitro synthesis of mmRNAs are pseudo-uridine and 5-methyl-cytosine. A key step in cellular mRNA processing is the addition of a 5' cap structure, which is a 5'-5' triphosphate linkage between the 5' end of the RNA and a guanosine nucleotide. The cap is methylated enzymatically at the N-7 position of the guanosine to form mature mCAP. When preparing ETV2 mmRNAs, a 5' cap is typically added prior to transfection of hPSCs in order to stabilize IF mmRNA and significantly enhance translation. In some embodiments a 4:1 mixture of a cap analog to GTP is used in transcription reactions to obtained 5'-capped mmRNAs. In preferred embodiments, the Anti Reverse Cap Analog (ARCA), 3'-O-Me-m7G(5')ppp(5')G is used to generate ETV2 mmRNAs that can be efficiently translated in hPSCs. Systems for in vitro synthesis are commercially available, as exemplified by the mRNAExpress™ mRNA Synthesis Kit (System Biosciences, Mountain View, CA).

ETV2 mmRNAs can be introduced into hPSCs by any of a number of established methods for transfection of mammalian cells, e.g., electroporation, nucleoporation, or lipofection.

In one exemplary embodiment ETV2 mmRNAs are introduced into hPSCs by nucleoporation as follows. Transfection of ETV2 mRNAs into hPSCs can be performed using a TransIT-mRNA reagent in E8 media containing ROCK inhibitor or electroporation. For example, single cell suspension was prepared using HyQtase (Thermo Fisher Scientific). Per one well of transfection, about $2 \times 10^5$ cells in 1 ml complete medium with 10 mM ROCK inhibitor (Y27632, StemCell Technologies, Vancouver Canada) plated into a collagen IV-coated 6-well plate and incubated by 30-60 minutes, and then mixture of 200 ng ETV2:TransIT-mRNA (Mirus Bio, Madison Wis.) added to each well according to the manufacturer's instructions. In another non-limiting example, the mmRNA is added by electroporation, for example, $10^6$ cells were nucleotransfected with 800 ng of mmETV2 in 100 µl of nucleofection buffer (Amaxa Human Stem Cell Nucleofector® Kit 2, Lonza) using Amaxa Nucleofector II B-016 program. After nucleofection, cells were divided equally between 4 wells of collagen IV-coated 6-well plates.

Rock inhibitor is a Rho kinase inhibitors, which are known in the art and include, but are not limited to, for example, Y27632 (commercially available from Stem Cell Technologies), and those found in Liao J K, Seto M, Noma K. Rho kinase (ROCK) inhibitors. J Cardiovasc Pharmacol. 2007; 50(1):17-24. doi:10.1097/FJC.0b013e318070d1bd, the contents of which are incorporated by reference in its entirety.

In other embodiments, ETV2 proteins are generated by in vitro translation and then transduced into hPSCs. In some cases, protein transduction method includes contacting cells with a composition containing a carrier agent and at least one purified polypeptide comprising the amino acid sequence of ETV2 (SEQ ID NO:4). Examples of suitable carrier agents and methods for their use include, but are not limited to, commercially available reagents such as Chariot™. (Active Motif, Inc., Carlsbad, Calif.) described in U.S. Pat. No. 6,841,535; Bioport®. (Gene Therapy Systems, Inc., San Diego, Calif.), GenomeONE (Cosmo Bio Co., Ltd., Tokyo, Japan), and ProteoJuice™. (Novagen, Madison, Wis.), or nanoparticle protein transduction reagents as described in, e.g., in U.S. Pat. No. 7,964,196.

The protein transduction method may comprise contacting hPSCs with at least one purified polypeptide comprising the amino acid sequence of ETV2 fused to a protein transduction domain (PTD) sequence (ETV2-PTD fusion polypeptide). The PTD domain may be fused to the amino terminal of an ETV2 sequence; or, the PTD domain may be fused to the carboxy terminal of an ETV2 sequence. In some cases, the ETV2-PTD fusion polypeptide is added to cells as a denatured polypeptide, which may facilitate its transport into cells where it is then renatured. Generation of PTD fusion proteins and methods for their use are established in the art as described in, e.g., U.S. Pat. Nos. 5,674,980, 5,652,122, and 6,881,825. See also, Becker-Hapak et al (2003), Curr Protocols in Cell Biol, John Wiley & Sons, Inc. Exemplary PTD domain amino acid sequences include, but are not limited to, any of the following: YGRKKRRQRRR; (SEQ ID NO:5); RKKRRQRR (SEQ ID NO:6) YARAAAR-QARA (SEQ ID NO:7); THRLPRRRRRR (SEQ ID NO:8); and GGRRARRRRRR (SEQ ID NO:9).

After introducing the ETV-2 into the PSCs, the ETV2-induced PSCs are cultured in serum-free, xenogen-free medium (e.g., StemLine II media) comprising FGF-2 for a suitable amount of time to produce a population of ETV2-induced CD144+hematoendothelial progenitor cells (ETV2-induced HEPs). The serum-free, xenogen-free medium preferably comprises about 10 ng/ml to about 50 ng/ml of FGF-2, for example, about 10 ng/ml to 30 ng/ml, for example 20 ng/ml. In some examples, the ETV2 induced PSCs are cultured on coated plates, for example, collagen coated plates (e.g., Collagen IV).

A sufficient amount of time for the first step (a) comprises culturing the ETV2-induced cells for about 3-8 days, for example, for about 4 days. For example, in some embodiments, step (a) comprises culturing for 3 day, alternatively 4 days, alternatively 5 days, alternatively 6 days, alternatively 7 days, alternatively 8 days to produce ETV2-induced CD144+thematoendothelial progenitor cells.

The ETV2-induced CD144+hematoendothelial progenitor cells are characterized by the expression on their surface of CD144 (CD144+), and do not express CD73, CD235a or CD43 (CD73$^-$CD235a$^-$/CD43$^-$).

The second step (b) comprises culturing the ETV2-induced CD144+hematoendothelial progenitor cells in serum- and xenogen-free medium comprising GM-CSF and FGF2 for a sufficient time to produce myeloid progenitors. In a preferred embodiment, the serum- and xenogen-free medium comprising GM-CSF, FGF-2 and UM171. As demonstrated in the examples, the addition at step (b) of UM171 in combination with GM-CSF and FGF-2 greatly improved the number of neutrophils produced by our serum-free and xenogen-free method.

In one example, the serum- and xenogen-free medium used in this second step (b) comprises about 10 ng/ml to about 200 ng/ml of GM-CSF; about 10 ng/ml to about 50 ng/ml FGF2; and optionally about 10 nM to about 100 nM UM171. In a preferred example, the serum-free and xenogen-free medium of the second step (b) comprises about 10 ng/ml to about 50 ng/ml of GM-CSF; about 10 ng/ml to about 50 ng/ml FGF2, and about 10 nM to about 100 nM UM171.

The second step (b) comprises culturing the cells for a sufficient amount of time to produce non-adherent myeloid progenitors (e.g., CD34+CD33+CD45+ myeloid progenitors), for example, at least 4 days, for example, at least 4-23 days.

The myeloid progenitors produced in step (b) are non-adherent (e.g., floating) blood progenitor cells that are characterized by the expression of CD45, CD43, CD34 and CD33 (CD45+CD43+CD34+CD33+) and lack expression of megakaryocytic and erythroid markers CD41 and CD235a (CD41$^-$CD235a$^-$). These non-adherent myeloid progenitors display typical myeloid progenitor morphology on cytospins and possess GM- and M-CFC potential, as demonstrated in FIGS. 2D and 2E. In some cases, these myeloid progenitor can also be classified as CD34+CD33+CD45+ myeloid progenitors or CD34+CD33+CD43+CD45+ myeloid progenitor cells, or called CD45+ myeloid progenitors, and these terms may be used interchangeably to represent the population of cells referred to as myeloid progenitors.

Methods of obtaining myeloid progenitor cells from human pluripotent stem cells (hPSCs) that are known in the art are contemplated for use in the methods described herein.

Step (b) produces a population non-adherent CD45+ myeloid progenitors that are more than 75% positive for the CD34 and/or CD33 markers, alternatively more than 80% positive for the CD34 and/or CD33 markers. If step (b) is carried out for longer than 8 days, the CD34 and CD33 marker begins to gradually decrease while the CD11b and CD16 marker of mature myeloid cells gradually increase in the floating cells.

Step (b) may further include, in some embodiments, a method of isolating the non-adherent CD45+ myeloid cells from the culture. Suitable methods of isolating the cells are known in the art. In one example, non-adherent cells can be collected from the culture leaving the adherent cells behind. In another example, non-adherent cells may be collected and stained (i.e., bound to antibodies) for one or more markers of myeloid cells (e.g., CD45, CD34, CD33, CD43) and sorted by FACS cell sorting. The isolated population may be at least 75% myeloid cells, alternatively at least 80%, alternatively at least 85%, alternatively at least 90%, alternatively at least 95%, alternatively at least 98% myeloid cells. In some embodiments, the adherent cells isolated from the non-adherent myeloid cells, may be used in methods of producing macrophages, as described in detail below.

The third step (c) comprises culturing the CD34+CD45+ myeloid progenitors in xenogen-free medium (e.g., StemSpan™ H3000, StemCell Technologies) comprising G-CSF and a retinoic acid agonist for a sufficient amount of time to differentiate the CD34+CD45+ myeloid progenitors and produce CD16+CD10$^-$ neutrophils. The serum-free, xenogen-free medium suitably comprises a sufficient amount of G-CSF and retinoic acid agonist to produce neutrophils from CD34+CD45+ myeloid progenitors. Suitable amounts of G-CSF and retinoic acid agonist include, for example, about 100 ng/ml to about 200 ng/ml of G-CSF, and about 1 µm to about 5 µM of the retinoic acid agonist. In another example, the ranges are about 120 ng/ml to about 180 ng/ml of G-CSF, and about 2 µm to about 4 µM retinoic acid agonist.

Suitable retinoic acid agonists, or retinoic acid receptor, alpha (RARα) agonists are known in the art and commercially available, and include, but are not limited to, for example, AM580, Adapalene, AM 80, BMS 753, BMS 961, CD 1530, CD 2314, CD 437, Ch55, Isotretinoin, Tazarotene, TTNPB, and retinoic acid, among others. In a preferred embodiment, the selective RAR₪ agonist is AM580.

Step (c) is performed for a suitable amount of time in order produce neutrophils from CD34+CD33+CD45+ myeloid progenitors by in vitro differentiation. In some examples, step (c) is carried out for at least 7 days, for example, at least 7-21 days.

The three-step method described above is advantageous in that neutrophils are produced at 14 days after initiating step (a) in pluripotent step cells. This is a rapid method for in vitro producing neutrophils in xenogen-free conditions which can be used for therapeutic purposes.

In some embodiments, the methods provide a population of greater than 50% in vitro produced neutrophils, alternatively at least 60%, alternatively at least 70%, alternatively at least 80% neutrophils are produced from the PSCs cells in the methods described (as determined by methods known in the art including, but not limited to, flow cytometry, histology or neutrophil marker expression). In one example, the methods provide neutrophils which are greater than 50% positive for CD16.

In some embodiments, the method produced neutrophils that were at least 80% neutrophils as determined by typical cellular morphology and neutrophil marker staining.

The methods described herein to use pluripotent stem cells to obtain neutrophils. Suitably, the pluripotent stem cells are induced pluripotent stem cells. In another suitable example, the pluripotent stem cells are embryonic stem cells. In some embodiments, the pluripotent stem cells can be genetically modified (genetically altered) with a gene of interest prior to differentiating in the methods described herein. For example, in some embodiments, the methods described herein use genetically modified induced pluripotent stem cells. This, in turn, allows for the production of genetically modified neutrophils, which differ from neutrophils obtained from a donor, as such neutrophils cannot be genetically modified Thus the present methods allow for the ability to produced genetically modifiable neutrophils. Genetic modification of neutrophils may be to generate neutrophils with improved characteristics, for example, improved anti-microbial or anti-tumor functions.

Methods of genetically modifying the pluripotent stem cells are known in the art. For example, the pluripotent stem cells may contain a expression vector capable of expressing the protein encoded by a gene of interest.

As used herein, the term "pluripotent cell" and "pluripotent stem cell" means a cell capable of differentiating into cells of all three germ layers. Examples of pluripotent cells include embryonic stem (ES) cells and induced pluripotent stem (iPS) cells. As used herein, "iPS cells" refer to cells that are substantially genetically identical to their respective differentiated somatic cell of origin and display characteristics similar to higher potency cells, such as ES cells, as described herein but contain exogenous transcription factors used to reprogram the cells. The cells can be obtained by reprogramming non-pluripotent (e.g., multipotent or somatic) cells by introducing products of specific sets of pluripotency-associated genes, or "reprogramming factors", into a given cell type. The original set of reprogramming factors (also dubbed Yamanaka factors) are the transcription factors Oct4 (PouSf1), Sox2, cMyc, and Klf4. While this combination is most conventional in producing iPSCs, each of the factors can be functionally replaced by related transcription factors, miRNAs, small molecules, or even non-related genes such as lineage specifiers. The iPSCs are cells that transiently express the reprogramming factors in order to gain pluripotency.

The present disclosure also provides for methods of producing neutrophils from a starting population of CD144+ thematoendothelial progenitor cells. The CD144+ hematoendothelial progenitor cells can be derived from pluripotent stem cells under serum-free conditions by methods known in the art, including the methods described above. In vitro derived neutrophils can be made by a method comprising (a) culturing CD144+thematoendothelial progenitor cells in xenogen-free medium comprising GM-CSF and FGF2 for a sufficient time to produce myeloid progenitors (e.g., CD34+CD33+CD4S+ myeloid progenitors); and (b) culturing the myeloid progenitors in xenogen-free medium comprising G-CSF and retinoic acid agonist to differentiate the myeloid progenitors into neutrophils. Conditions as discussed above for the three step process may be used for this method. It is understood that the CD144+ hematoendothelial progenitor cells may be derived from PSCs by the methods described herein or by other methods known in the art. In some embodiments, the CD144+ hematoendothelial progenitor cells may be isolated from a differentiating and culture of pluripotent stem cells by methods known in the art, for example, FACS sorting based on CD144+ phenotype, along with other cell surface markers, described above.

As used herein, the terms "chemically-defined culture conditions," "fully defined, growth factor free culture conditions," and "fully-defined conditions" indicate that the identity and quantity of each medium ingredient is known and the identity and quantity of supportive surface is known. Xenogen-free medium refers to medium that does not contain any components derived from animal or human sources, such as, for example, serum.

The methods described herein have many advantages of the methods described in the prior art. One advantage is that the methods are performed under xenogen-free conditions, specifically, under serum-free, xenogen-free conditions without feeder cells and without embryoid body formation. This allows for the scaling up and producing clinical grade cell populations that can be used as human therapeutics and produce GMP-compliant cells via a GMP-compliant manufacturing protocol.

In Vitro Derived Neutrophil Populations and Compositions

In some embodiments, a population of in vitro derived neutrophils produced by the method described herein are provided. As discussed above, the neutrophils produced by the methods described herein have characteristics of naturally found neutrophils (morphology, phagocytotic behavior, ROS activity, etc.) but are CD10 negative (CD10$^-$), which is not a characteristic of naturally found neutrophils. Not to be bound by any theory, but it is also believed that the neutrophils produced in vitro have characteristics different from primary derived neutrophils, for example, the in vitro derived neutrophils are believed to be less efficient at performing NETosis (i.e. form neutrophil extra-cellular traps (NETs) less efficiently compared to peripheral blood neutrophils). This reduction in the ability to perform NETosis and to form NETs may be advantageous when the in vitro derived neutrophils are used for therapeutic purposes, such as treatment of infections or cancer.

Figure 3:
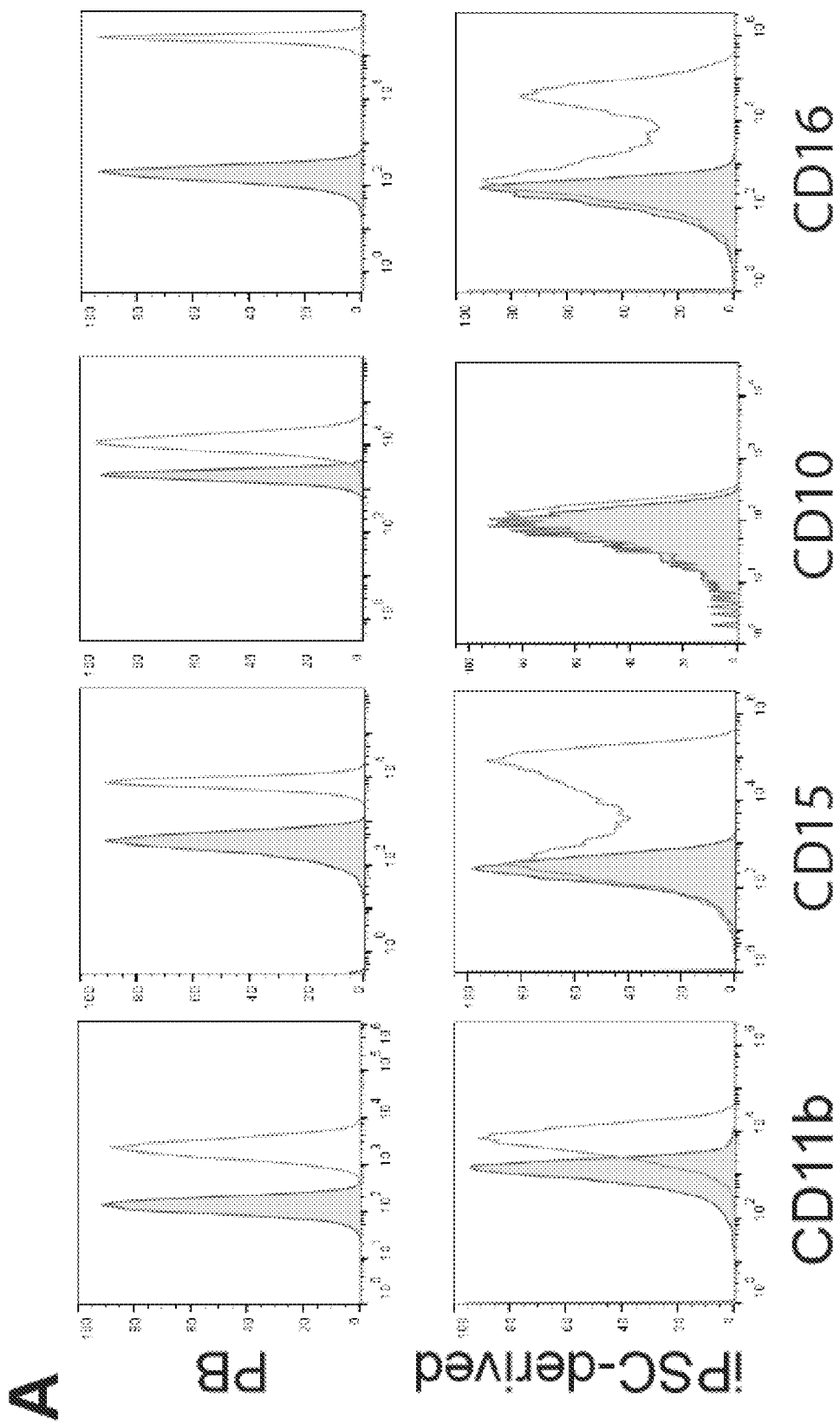
FIG. 3. Induction of neutrophil formation from myeloid progenitors. (A) Flow cytometric analysis of generated neutrophils. Plots show unstained control (red) and specific antibody (blue) histograms. (B) Cytospin showing the morphology of the generated neutrophils. Scale bar is 100 μm (main image) and 10 μm (insert). (C) Neutrophil yields from 106 myeloid progenitors which were cultured with or without UM171 and collected on day 8 of post-ETV2 mmRNA transfection. Bars show mean±SE for 3 (GM,FGF,U) and 2 (GM,FGF) independent experiments. (D) Total number of neutrophils obtained from 106 myeloid progenitors which were cultured with UM171 and collected at different days of post-ETV2 mmRNA transfection. Bars show mean±SE for 2 independent experiments. (E) Phagocytosis of pHrodo Green E. coli particles by neutrophils generated from IISH2i-BM9 hiPSCs. Solid red peaks on flow graphs are control cells incubated on ice with bio-particles, blue traces are cells containing acidified, fluorescent E. coli bio-particles from 370 C incubation. Bar graph is from 3 independent experiments showing percent of cells from 370 C incubation with phagocytosed acidified E. coli bio-particles. Bars show mean±SE. Difference between iPSC and primary neutrophils is not statistically significant ($p=0.3134$) as determined by unpaired t test. (F) ROS production of hiPSC-derived neutrophils compared to primary blood neutrophils at 90 minutes. Bar graph is from 3 independent experiments showing fold increase of 50 ng/ml PMA treated cells over control treated cells. Bars show mean±SE. Difference between hiPSC vs primary neutrophils is not statistically significant ($p=0.7522$) as determined by unpaired t test.
Figure 3:
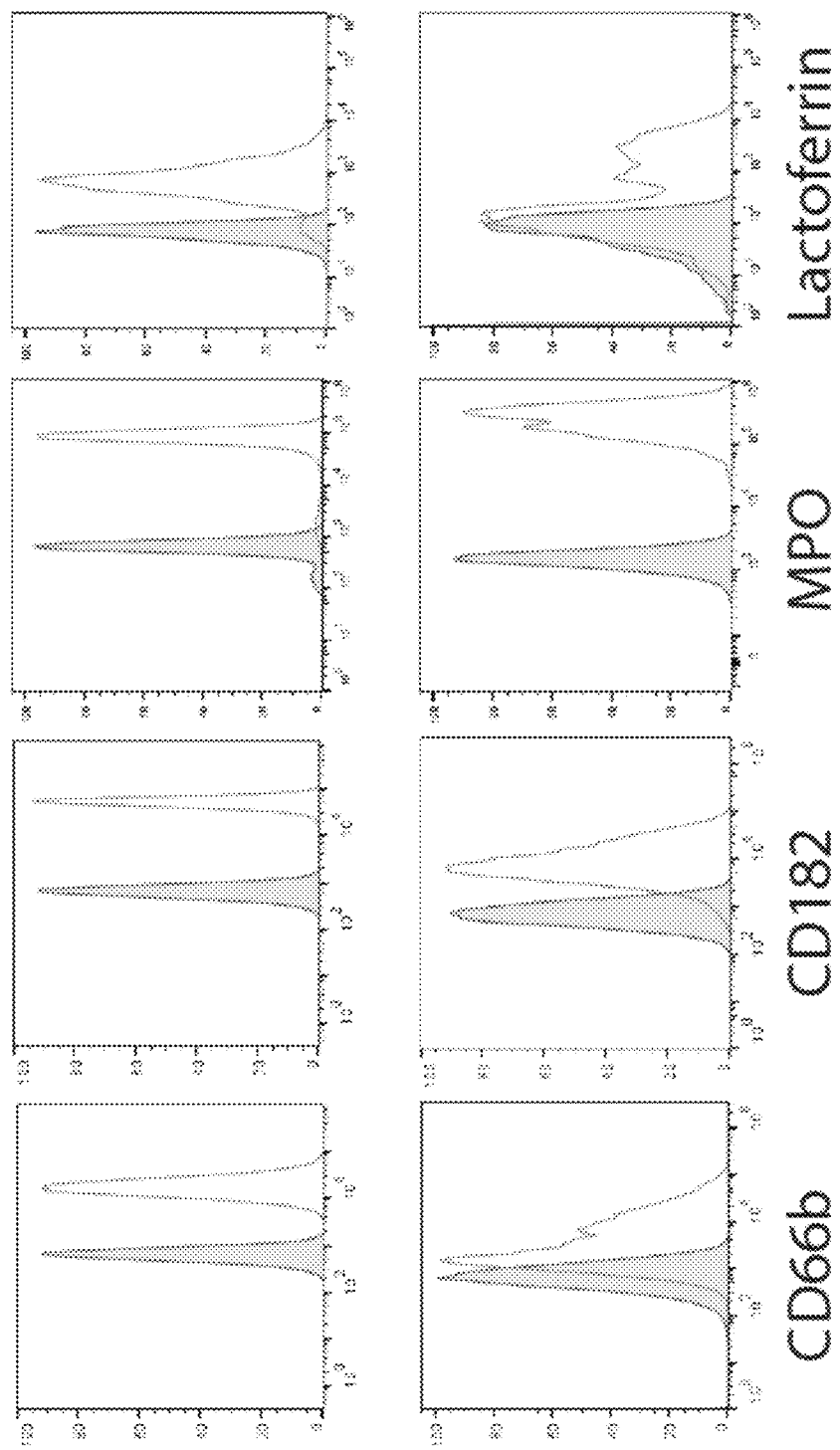
Figure 3:
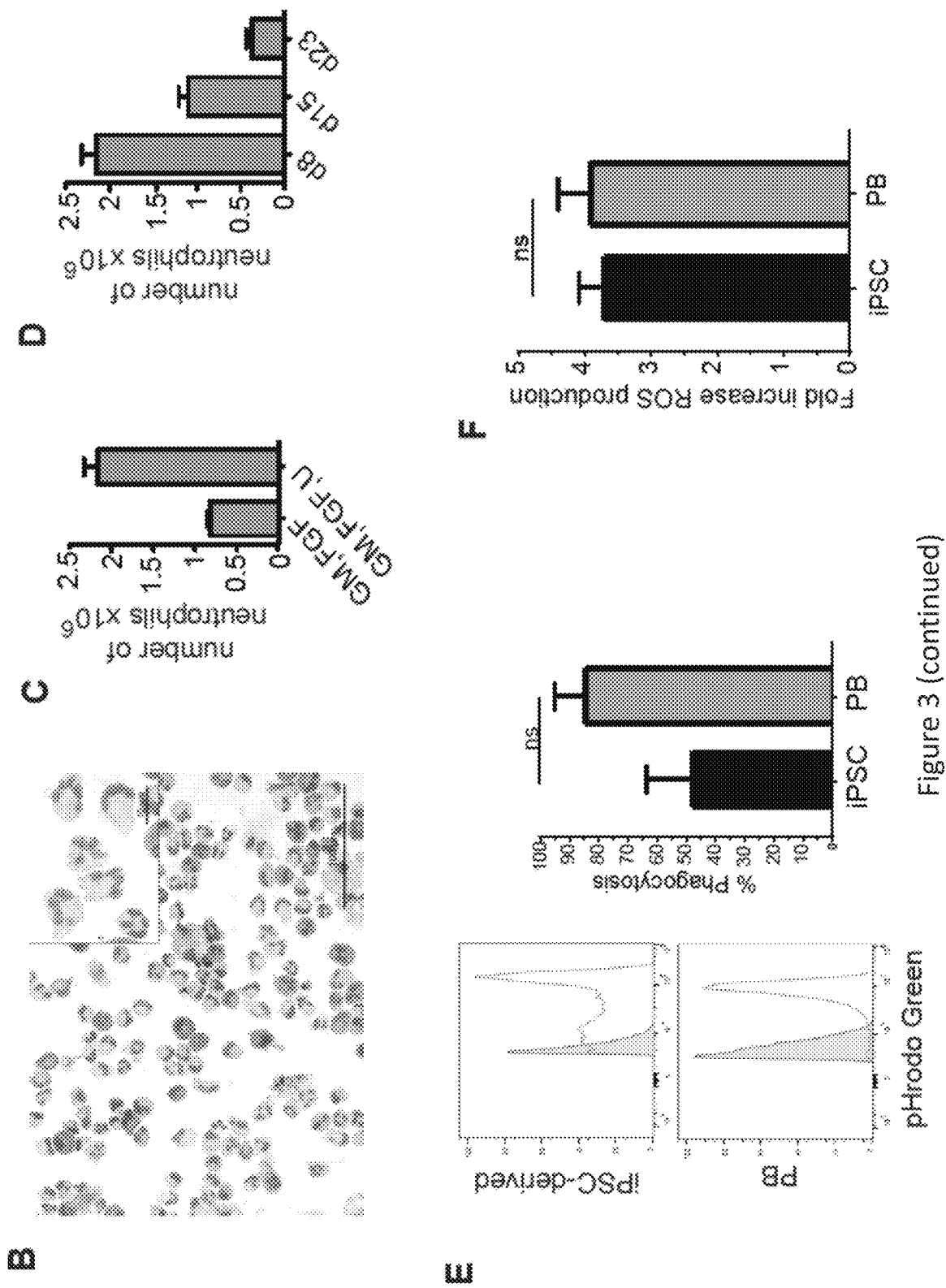

The neutrophils produced by the methods described herein express one or more of the following neutrophil marker CD11b, CD16, CD15, MPO, CD182, CD66b, and lactoferrin and do not express CD10, signifying an unique in vitro derived population of neutrophils (i.e., CD16$^+$CD10$^-$ neutrophils). The in vitro derived neutrophils are not found naturally, the fact that the neutrophils derived have a CD10$^-$ (i.e. lack CD10 expression) and CD66$^{low}$phenotype is unique to the in vitro derived serum-free, xenogen-free methods described herein. The neutrophils display neutrophil morphology and functional properties of somatic neutrophils, including, for example, efficient production of reactive oxygen species, phagocytosis, and a capacity to migrate in response to fMLP and IL10. Neutrophils can be detected by histological staining and flow cytometry using forward and side scatter, as neutrophils have a distinct phenotype and can readily be distinguished from other blood cells (macrophages and lymphocytes) by flow cytometry just by size as readily understood by one skilled in the art. Further, neutrophils have a distinct morphology, as they are non-adherent cells which has a nucleus divided into 2-5 lobes which can be readily detected by histological staining, as shown in FIG. 3B (demonstrating the multi-lobed nucleus stained). The population of neutrophils produced by the methods described herein also have phagocytic, chemotactic and signaling functions of primary human neutrophils. The neutrophils derived were also able to release reactive oxidative species (ROS) following activation.

The neutrophils and population of neutrophils made by the methods describe herein can be made as GMP-compliant cells via a GMP-compliant manufacturing protocol as the methods do not use xenogenic material or serum.

The present disclosure also provides populations of genetically modified CD16$^+$CD10$^-$ neutrophils as described above. The neutrophils may be genetically modified to expressed one or more genes of interest by modifying the pluripotent stem cell from which it is derived. These populations of genetically modified CD16⁺CD10⁻ neutrophils can be used in methods of treating particularly diseases in which the gene of interest would provide benefits to the subject being treated. This is an advantage over primary neutrophils that are derived from a donor as primary neutrophils cannot be genetically modified. For example, the neutrophils may be modified to improve microbial killing functions or improve tumor cell killing.

The neutrophils may be produced and cryopreserved for later use for administering to a subject. Suitable medium and methods for cryopreservation of cells for therapeutic use is known in the art, and include, a cryopreservation solution and freezing and storing the cells at −135° C. or colder (i.e., in liquid nitrogen). Cells can be thawed and resuspended in a suitable pharmaceutically acceptable carrier before administration to a subject. For example, the neutrophils may be produced and stored for later off the shelf use.

Although neutrophil extracellular traps (NETs) protect against infection, they also stimulate thrombosis, organ damage, autoimmunity and cancer metastasis. Generation of neutrophils which are less prone to NET formation may provide a safer product for cellular therapies of conditions in which NET activation is undesirable, including sepsis and coagulopathies. The in vitro derived $CD16^+CD10^-$neutrophils produced by the methods described herein have a reduce ability to form NETs may provide benefits in the treatment of cancer and infections by reducing the detrimental side effects of neutrophils engaging in NETosis, e.g., inflammation, thrombosis, organ failure, metastasis, among others.

The present disclosure also provides compositions, preferably GMP-compliant compositions comprising the neutrophils described herein and a pharmaceutically acceptable carrier. The pharmaceutically acceptable carrier is preferably a carrier that maintains the viability of the cells and is acceptable for human administration. Suitable carriers include carriers that are suitable for the growth, stability, and/or maintenance of the cells and maintaining their differentiated phenotype.

As used herein, "pharmaceutically acceptable carrier" refers to liquid and solid carriers, vehicles, fillers, diluents, encapsulating material, or excipients used in the art for production and delivery of pharmaceutical compositions. Pharmaceutically acceptable carriers are typically non-toxic and inert. A pharmaceutically acceptable carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, pharmaceutically acceptable salts, wetting agents, or other biocompatible materials. A tabulation of ingredients listed by the above categories, may be found in the U.S. Pharmacopeia National Formulary, 1857-1859, (1990).

Methods of Making Macrophages

In vitro method of producing $CD14^+CD16^+$ macrophages from pluripotent stem cells (PSCs) is also provided. The method comprises (a) transiently introducing exogenous ETV2 into pluripotent stem cells and culturing the ETV2-induced PSCs in xenogen- and serum-free medium comprising FGF2 to produce ETV2-induced $CD144^+$hematoendothelial progenitor cells; (b) culturing the ETV2-induced $CD144^+$thematoendothelial progenitor cells in xenogen- and serum-free medium comprising GM-CSF and FGF-2 and optionally UM171 for about 4 days, and isolating the adherent cells from the culture, and (c) culturing the adherent cells of step (b) in serum-containing medium comprising IL-3 and M-CSF to produce the $CD16^+$ mature macrophages. Step (a) in this method is the same as the step for producing neutrophils; however, step (b) involves isolating the adherent cells (as opposed to the non-adherent cells that differentiate into neutrophils), and the conditions for the third step differ as this step involves conditions required to derive monocyte/macrophage population.

The macrophages/produced by the methods are characterized by exhibiting macrophage morphology. The term macrophages, as used herein, encompasses monocytes, which are macrophages that circulate in the peripheral blood. Macrophages and monocytes have characteristic morphology. Monocytes are large, spherical cell with prominent surface ruffles and blebs and the cytoplasm containing scattered granules when examined by microscopy. The archetypal geometry of the monocyte nucleus is ellipsoidal (bean-shaped or kidney-shaped) containing unilobar nuclei. Monocytes are found in the blood while macrophages are the differentiated form of monocytes within tissue. Macrophages have a prominent electron-dense membrane-bound lysosomes.

The xenogen- and serum-free medium in step (b) of macrophage derivation comprises about 10 ng/ml to about 200 ng/ml of GM-CSF; about 10 ng/ml to about 50 ng/ml FGF2; and the medium of step (c) comprises about 10-100 ng/ml of IL-3; and about 10-200 ng/ml of M-CSF, preferably xenogen-free medium. Step (c) culturing step is performed for at least 7 days, for example, for 7-14 days.

Step (b) further includes a step of isolating the adherent cells from the non-adherent cells. Methods of isolating the adherent cells are known in the art. For example, the tissue culture well may be forcefully rinsed with PBS or tissue culture medium or treated with EDTA-containing Calcium and Magnesium-free phosphate-buffered saline(PBS) such as Versene or others in order to remove and dislodge any non-adherent cells.

The method can be used to derive an in vitro derived $CD14^+CD16^+$ macrophages population that can be used for laboratory and clinical applications.

In Vitro Derived Macrophage Populations

The present disclosure further provides in vitro derived populations of $CD14^+CD16^+$ macrophages which can be used for therapeutic purposes. These in vitro derived macrophages can be used to enhance immune system, for example, to help clear infections or malignant cells from a subject in need thereof.

The macrophages produced by the methods are characterized by exhibiting monocyte/macrophage morphology and expression of one or more macrophage marker. Monocytes are large, spherical cell with prominent surface ruffles and blebs and the cytoplasm containing scattered granules when examined by microscopy. The archetypal geometry of the monocyte nucleus is ellipsoidal (bean-shaped or kidney-shaped) containing unilobar nuclei. Monocytes are found in the blood while macrophages are the differentiated form of monocytes within tissue. Macrophages have prominent electron-dense membrane-bound lysosomes. Methods of identifying monocytes and macrophages are known in the art, including, for example, by flow cytometry.

The macrophages produced by the methods described herein are CD14, CD16, CD163 and CD68 and CD80 positive. In some embodiments, an isolated in vitro derived population of greater than 50% in vitro produced $CD16^+$ $CD14^+$ macrophages, alternatively at least 60% $CD16^+$ $CD14^+$ macrophages, alternatively at least 70% $CD16^+$ $CD14^+$ macrophagess, alternatively at least 80% $CD16^+$ $CD14^+$ macrophages are produced in the methods described (as determined by methods known in the art including, but not limited to, flow cytometry, histology or monocyte marker expression). In one example, the methods provide a population of macrophages that are greater than 50% positive for CD14. Any of these populations of macrophages are also positive for CD68, CD80 and CD163.

Therapeutic Use

The in vitro derived neutrophils can be used in methods of treating a patient in which the patient is in need of neutrophils. The neutrophils can be formulated into a clinical grade formulation that can be administered to a subject in an effective amount to treat a condition in which neutrophils are beneficial.

In one embodiment, the neutrophils can be used for combating diseases caused by the condition of immunodeficiency resulting from or associated with neutrophil dysfunction or neutropenia. Neutropenia is a decrease in circulating neutrophils in the nonmarginal pool, which constitutes 4-5% of total body neutrophil stores. Granulocytopenia is defined as a reduced number of blood granulocytes, namely neutrophils, eosinophils, and basophils. However, the term granulocytopenia is often used synonymously with neutropenia and in that case is confined to the neutrophil lineage alone.

Mild neutropenia is present when the absolute neutrophil count (ANC) is 1000-1500 cells/A, moderate neutropenia is present with an ANC of 500-1000/4, and severe neutropenia refers to an ANC lower than 500 cells/µL. The risk of bacterial and fungal infection is related to both the severity and duration of the neutropenia. The risk of serious infection increases as the absolute neutrophil count (ANC) falls to the severely neutropenic range (<500/µL). The duration and severity of neutropenia directly correlate with the total incidence of all infections and of those infections that are life threatening. When neutrophil counts fall to <500/µL, endogenous microbial flora (e.g., in the mouth or gut) can cause infections. If the count falls to <200/µL, the inflammatory response may be muted and the usual inflammatory findings of leukocytosis or WBCs in the urine or at the site of infection may not occur. Acute, severe neutropenia significantly impairs the immune system and can lead to rapidly fatal infections.

In one embodiment, the neutrophils can be used for treating neutropenia, the method comprising administering an effective amount of the neutrophils derived herein to treat the neutropenia.

In another embodiment, the neutrophils can be used for treating chemotherapy-induced neutropenia. Cancer chemotherapy is the most common cause of neutropenia. Other cancer treatments, including radiation therapy, stem cell or bone marrow transplants, or steroids (which usually actually raise the neutrophil count, but still increase the risk of infection), can also lower neutrophil count. Methods of treating chemotherapy-induced neutropenia are contemplated. The methods comprise administering an effective amount of the neutrophils described herein to treat the chemotherapy-induced neutropenia within a subject.

In some examples, treating the chemotherapy-induced neutropenia or neutropenia is characterized by the increase in the number of circulating neutrophils within the subject as compared to prior to administration of the cells.

In one embodiment, the neutrophils can be used for effectively reducing the time to ANC recovery, days of leukopenia, and days of neutropenia.

Suitable types of neutropenia that can be treated by the methods described herein, include but are not limited to, chronic benign neutropenia, chronic idiopathic neutropenia, severe congenital neutropenia (SCN, or Kostmann syndrome), cyclic neutropenia, neutropenia, secondary neutropenia, among others.

Secondary neutropenia that can be treated by the methods described herein, particularly, administering an effective amount of the neutrophils described herein to treat the secondary neutropenia. The cause of the secondary neutropenia is one known in the art, including, for example, but not limited to, neutropenia produced certain drugs, bone marrow infiltration or replacement, certain infections, or immune reactions, among others. Drug-induced neutropenia is caused by drugs that can decrease neutrophil production through toxic, idiosyncratic, or hypersensitivity mechanisms. Severe dose-related neutropenia occurs predictably after cytotoxic cancer drugs or radiation therapy due to suppression of bone marrow production. Thus, the neutrophils described herein can be used to treat drug-induced neutropenia, including chemotherapy-induced neutropenia. In some embodiments, the neutrophils are administered co-currently with drug treatment. In other examples, the neutrophils are administered one or more times after drug treatment in order to replenish the neutrophils within the subject.

Other symptoms of neutropenia that can be treated by the methods described herein in a subject include, but are not limited to, for example, bacterial infections, stomatitis, gingivitis, perirectal inflammation, colitis, sinusitis, paronychia, and otitis media often occur. Patients with prolonged neutropenia after hematopoietic stem cell transplantation or chemotherapy and patients receiving high doses of corticosteroids are predisposed to fungal infections.

The present disclosure also provides methods of treating infection, the method comprising administering an effective amount of the neutrophils described herein to treat the infection. In some embodiments, the neutrophils are administered in an effective amount to reduce or inhibit the growth or kill the pathogen causing the infection, for example, a bacteria or fungus. Neutrophils actively attack a pathogen by producing a respiratory burst; exposing the pathogenic cell to hydrogen peroxide, free radicals, and hypochlorite and are phagocytic, able to engulf and then degrade pathogenic cells. The term pathogenic cells refers to either the pathogen cell (e.g., bacteria cell or fungal cell) or a cell that has been infected by a pathogen (e.g., virally infected cell). In other examples, the neutrophils are administered in an effective amount to reduce, inhibit or kill a viral-infected cells in order to reduce the viral load in the subject. The present disclosure contemplates the ability of the in vitro derived neutrophils described herein to be able to reduce, inhibit or kill a pathogen (e.g., bacteria or fungus) by functioning in vivo within the subject to provide a respiratory burst or phagocytosis of the pathogen. Any suitable infection are able to be treated by the methods described herein, including infections associated with neutropenia.

As discussed above, the in vitro derived CD10-neutrophils may also be used in methods in which there is a need to reduce the side effects of neutrophils formation of NETs, as the neutrophils derived by the methods described herein have a reduced or impaired ability to form neutrophil extracellular traps (NETs). This may be important to reduce the side effects of using neutrophils to treat subjects (e.g., treating infection or cancer) but reducing the unwanted side effects, for example, reducing the ability of the NETS to stimulate thrombosis, organ damage, autoimmunity and cancer metastasis. Not to be bound by any theory, but it is believed that the neutrophils of the present invention are less prone to NET formation will provide a safer product for cellular therapies of conditions in which NET activation is undesirable, including sepsis and coagulopathies.

Common infections associated with neutropenia include, but are not limited to, for example, cellulitis, furunculosis, pneumonia, septicemia, among others. Some common bacterial causes of skin infections (cellulitis) include, but are not limited to, for example, coagulase-negative staphylococci and *Staphylococcus aureus*, and include other gram-positive and gram-negative bacteria.

As discussed above, the in vitro derived CD10-neutrophils may also be used in methods in which there is a need to reduce the side effects of neutrophils formation of NETs, as the neutrophils derived by the methods described herein have a reduced or impaired ability to form neutrophil extracellular traps (NETs). This may be important to reduce the side effects of using neutrophils to treat subjects (e.g., treating infection or cancer) but reducing the unwanted side effects, for example, reducing the ability of the NETS to stimulate thrombosis, organ damage, autoimmunity and cancer metastasis. Not to be bound by any theory, but it is believed that the neutrophils of the present invention are less prone to NET formation will provide a safer product for cellular therapies of conditions in which NET activation is undesirable, including sepsis and coagulopathies.

In another embodiment, the present disclosure provides methods of treating wounds or burns, the methods comprising contacting the wound or burn with an effective amount of the neutrophils of the present disclosure to treat the wound or burn. In some embodiments, the neutrophils are contacted topically with the wound or burn, for example, by topical application or application on a wound dressing or bandage. Other methods of administering to treat a burn or wound include systemic administration, for example, intravenously. In some embodiments, the present disclosure provides methods of treating or inhibiting a pathogenic infection associated with a wound or burn, the method comprising administering an effective amount of the neutrophils described herein to inhibit or treat the pathogenic infection (e.g., reduce the number of pathogens associated with the burn or wound, inhibit growth of the pathogen associated with the wound or burn, etc.). In a preferred embodiment, the pathogen is a bacterial pathogen, particularly a pathogen associated with cellulitis.

In a further embodiment, the neutrophils described herein may be used in methods of treating sepsis, the methods comprising administering an effective amount of the neutrophils to treat the sepsis, and also to reduce unwanted side effects of neutrophils, e.g., reduce the NETosis caused by the administered neutrophils.

In a further embodiment, genetically modified neutrophils are used to treat a subject in need thereof, for example, subject being treated for cancer or infection. In some embodiments, the subject is a neutropenic subject. Type of infections include, but are not limited to, for example, bacterial and fungal infections.

For purposes of the present invention, "treating" or "treatment" describes the management and care of a subject for the purpose of combating the disease, condition, or disorder. Treating includes the administration of cells of present invention to prevent the onset of the symptoms or complications, alleviating the symptoms or complications, or eliminating the disease, condition, or disorder. The aim of treatment includes the alleviation of symptoms, slowing or stopping the progression or worsening of a disease, disorder, or condition and/or the remission of the disease, disorder or condition.

The present invention also provides populations of in vitro derived $CD14^+CD16^+$ macrophages that may be used for the treatment of subjects in need thereof. For example, the in vitro derived $CD14^+CD16^+$ macrophages may be used to treat cancer, a disease associated with macrophage dysfunction or in diseases in which the immune system is imbalanced, such as, for example, neurodegenerative, cardiovascular, metabolic, respiratory, autoimmune and musculoskeletal diseases. For example, some diseases that may be treated with macrophages include, for example, solid cancers (ovarian, gastric, lung pancreatic), chronic wounds, central nervous system injury, pulmonary alveolar proteinosis, among others.

Suitable routes of administering the cells of the present disclosure are known in the art and include, but are not limited to, topical administration, parenteral administration, for example intravenously or by transfusion, among others. The route of administration will depend on the condition being treated. For example, for treating neutropenia, cells may be administered parenterally, for example, intravenously.

The amount and timing of administration are at the discretion of the treating clinician to achieve the desired outcome. The cells can be formulated in a composition for systemic (such as intravenous, intrathecal) or local (topical) administration depending on the specific disease or disorder being treated. In one example, the cells are formulated for parenteral administration, such as intravenous administration.

The term "effective amount" or "therapeutically effective amount" refers to an amount sufficient to effect beneficial or desirable biological and/or clinical results.

The cells may be formulated into a composition suitable for administration to a subject, for example, in a pharmaceutically acceptable carrier. Such pharmaceutically acceptable carriers will be carriers that will maintain the viability of the cells before administration. Pharmaceutically acceptable" carriers are known in the art and include, but are not limited to, for example, suitable diluents, preservatives, solubilizers, emulsifiers, liposomes, nanoparticles and the like. Pharmaceutically acceptable carriers are well known to those skilled in the art and include, but are not limited to, 0.01 to 0.1 M and preferably 0.05M phosphate buffer or 0.9% saline. Additionally, such pharmaceutically acceptable carriers may be aqueous or non-aqueous solutions, suspensions, and emulsions. Examples of nonaqueous solvents are propylene glycol, polyethylene glycol, vegetable oils such as olive oil, and injectable organic esters such as ethyl oleate. Aqueous carriers include isotonic solutions, alcoholic/aqueous solutions, emulsions or suspensions, including saline and buffered media. Water is not contemplated as a suitable physiologically acceptable carrier. In some embodiments, additional components may be add to preserve the structure and function of the cells of the present invention, but are physiologically acceptable for administration to a subject.

As used herein "subject" or "patient" refers to mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Preferably, the subject is a human. In some embodiments, the subject is a subject having neutropenia or an infection. The term "subject" does not denote a particular age or sex. In one specific embodiment, a subject is a mammal, preferably a human.

As used herein, "about" means within 5-10% of a stated concentration range or within 5-10% of a stated number.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit's interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting examples.

EXAMPLES

Example 1

This Example demonstrates human induced pluripotent stem cells (hiPSCs) serve as a versatile and scalable source of neutrophils, which when coupled with genetic engineering technologies can be used to meet specific clinical needs. Here, the inventors describe a rapid efficient feeder- and xenogen-free protocol for neutrophil generation from hiPSCs, which is based on direct hematoendothelial programming of hiPSCs using ETV2 modified mRNA. Culture of ETV2-induced hematoendothelial progenitors in the presence of GM-CSF, FGF2 and UM171 led to continuous production of generous amounts of CD34+CD33+CD4S+ myeloid progenitors which could be harvested every 8-10 days for up to 30 days of culture. Subsequently, myeloid progenitors were differentiated into neutrophils in the presence of G-CSF and the retinoic acid agonist Am580. Neutrophils obtained in these conditions displayed a typical somatic neutrophil morphology, produced reactive oxygen species, and possessed phagocytic and chemotactic activities. In addition, we demonstrated that culture of ETV2 modified mRNA transduced cells with GM-CSF followed by culture with IL-3 and M-CSF produce macrophages. In some embodiment, the medium comprises about 10 ng/ml to 100 ng/ml IL3 and 10 ng/ml to about 200 ng/ml M-CSF. Overall, this technology offers an opportunity to generate a significant number of neutrophils and monocyte/macrophages in GMP-compatible conditions for cell- and gene-therapy applications.

Human induced pluripotent stem cells (hiPSCs) offer the potential to serve as a versatile and scalable source of granulocytes, which could be coupled with genetic engineering technologies to meet specific clinical needs. Although our group and others have demonstrated feasibility of neutrophil generation from hiPSCs[8-12], previously described methods rely on the use of serum, feeder or embryoid body formation, which hampers their adoption for GMP manufacturing and clinical use. In present studies, we have developed a 3 step protocol for efficient neutrophil production from hiPSCs in 2D, serum- and feeder-free conditions using direct programming with modified mRNA (mmRNA). Initially, hiPSCs are directly programmed into hematoendothelial progenitors using ETV2 mmRNA which then differentiated into myeloid progenitors in the presence of GM-CSF, FGF2 and UM171. Myeloid progenitors could be continuously collected from cultures every 8-10 days for up to 30 days of post ETV2 transfection, and subsequently differentiated into mature neutrophils in the presence of G-CSF and the retinoic acid agonist Am580. This method significantly expedites generation of neutrophils with the first batch of neutrophils available as soon as 14 days after initiation of differentiation and allows the generation of up to $1.7 \times 10^7$ neutrophils from $10^6$ hPSCs. The proposed differentiation system may be suitable for generating mature functional granulocytic cells for correction of neutropenia and gene therapies.

Induction of Hematoendothelial Program with Myeloid Potential by ETV2 mmRNA

Figure 7:
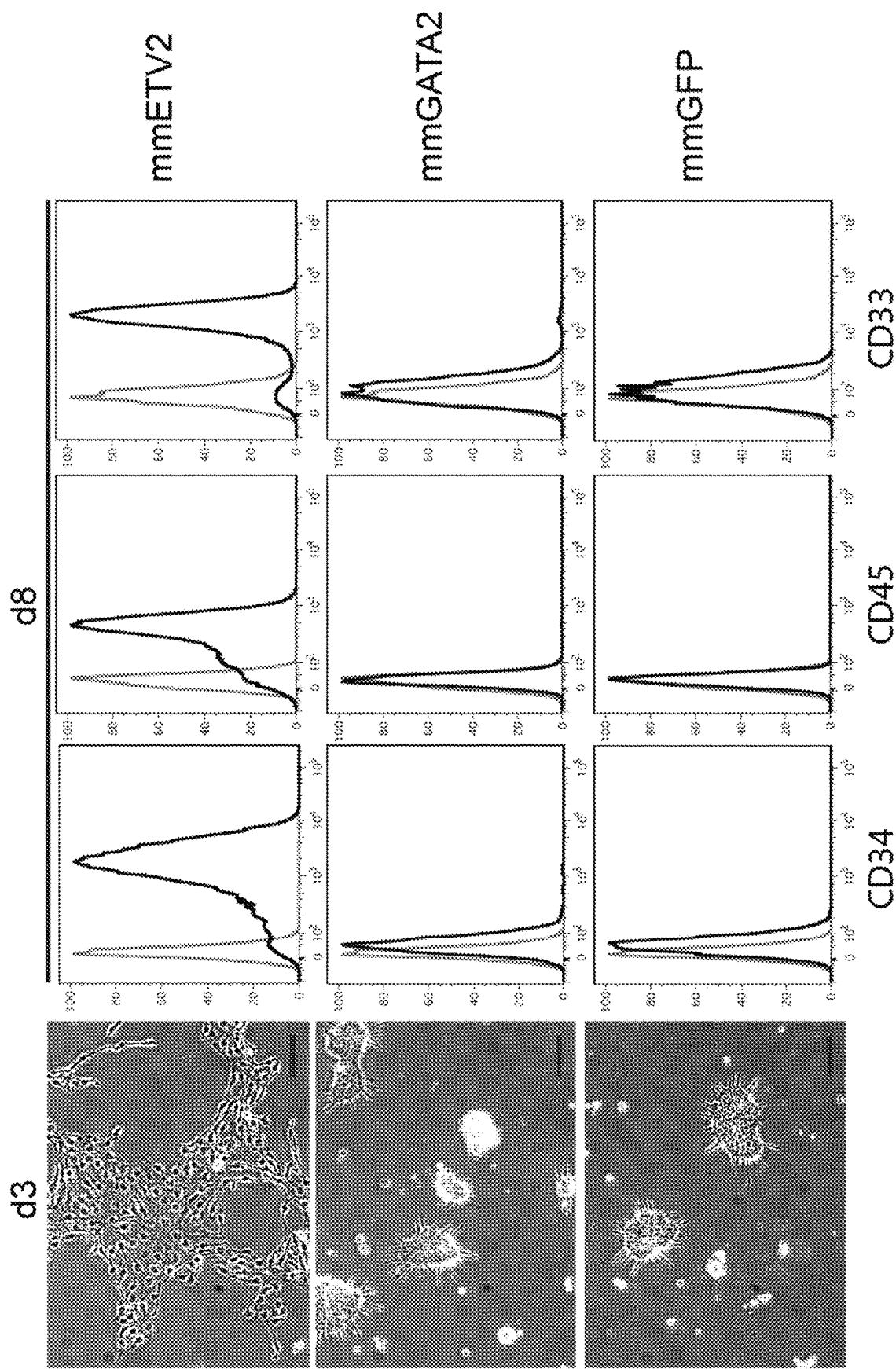
FIG. 7. Induction of myeloid progenitors is specific for ETV2 modified mRNA. iPSCs were transfected with ETV2, GATA2 or GFP modified RNA and cultured as outlined in FIG. 1A. Formation of CD34+CD45+CD45+ myeloid progenitors was observed only in ETV2 mmRNA transfected cultures.

Previously, we demonstrated that overexpressing transcription factors ETV2 and GATA2 is sufficient to induce a pan-myeloid program in hiPSCs, which proceeds through a hemogenic endothelium (HE) stage[13]. Although we have found that constitutive overexpression of ETV2 using lentiviral vectors induces predominantly non-hemogenic endothelium, we also noted that ETV2 induces GATA2 expression in hPSCs and very few HE with macrophage potential[13]. In addition, our recent studies suggest that molecular mechanisms upstream of GATA2 are sufficient to specify hematoendothelial program in hPSCs, while GATA2 is required for endothelial-to-hematopoietic transition (EHT)[14]. Given these findings and studies demonstrating the critical role of ETV2 threshold for hematoendothelial commitment[15] and obligatory downregulation of ETV2 during subsequent stages of hematopoietic development in the embryo[16], we explored whether transitional expression of ETV2 with mmRNA alone is sufficient for hematoendothelial programming in hiPSCs. For ETV2 mmRNA production we used transcription template which contains single 5'UTR and single 3'UTR from β globin gene. In prior studies, we found that mmRNA in this configuration provides maximum protein levels in hPSCs (Sihnuntha et al., 2018). Overexpression of mmETV2 following culture of transfected hiPSCs in StemLine II serum-free medium with FGF2, rapidly induces CD144+ expressing endothelial cells that, upon addition of GM-CSF, form floating CD43+ blood cells most of which coexpress CD45 (FIG. 1A-1E). Transfection of cells with GFP or GATA2 mmRNA was unable to induce hematopoietic program in these conditions, indicating that this effect is specific for ETV2 and is not an artifact of the mmRNA transfection procedure (FIG. 7). Interestingly, as soon as the first floating cells appeared (starting on day 5 post-ETV2 treatment), some of them began to adhere and continue producing floating blood cells for another 2 weeks (FIG. 1B), thereby allowing for continuous collection of blood cells for up to three weeks of culture. Typically, around $0.9 \times 10^6$, $1.25 \times 10^7$ and $2 \times 10^6$ floating blood cells can be collected after the $1^{st}$, $2^{nd}$ and $3^{rd}$ weeks, accordingly from $10^6$ hiPSCs transfected with ETV2 (FIG. 1F).

Figure 2:
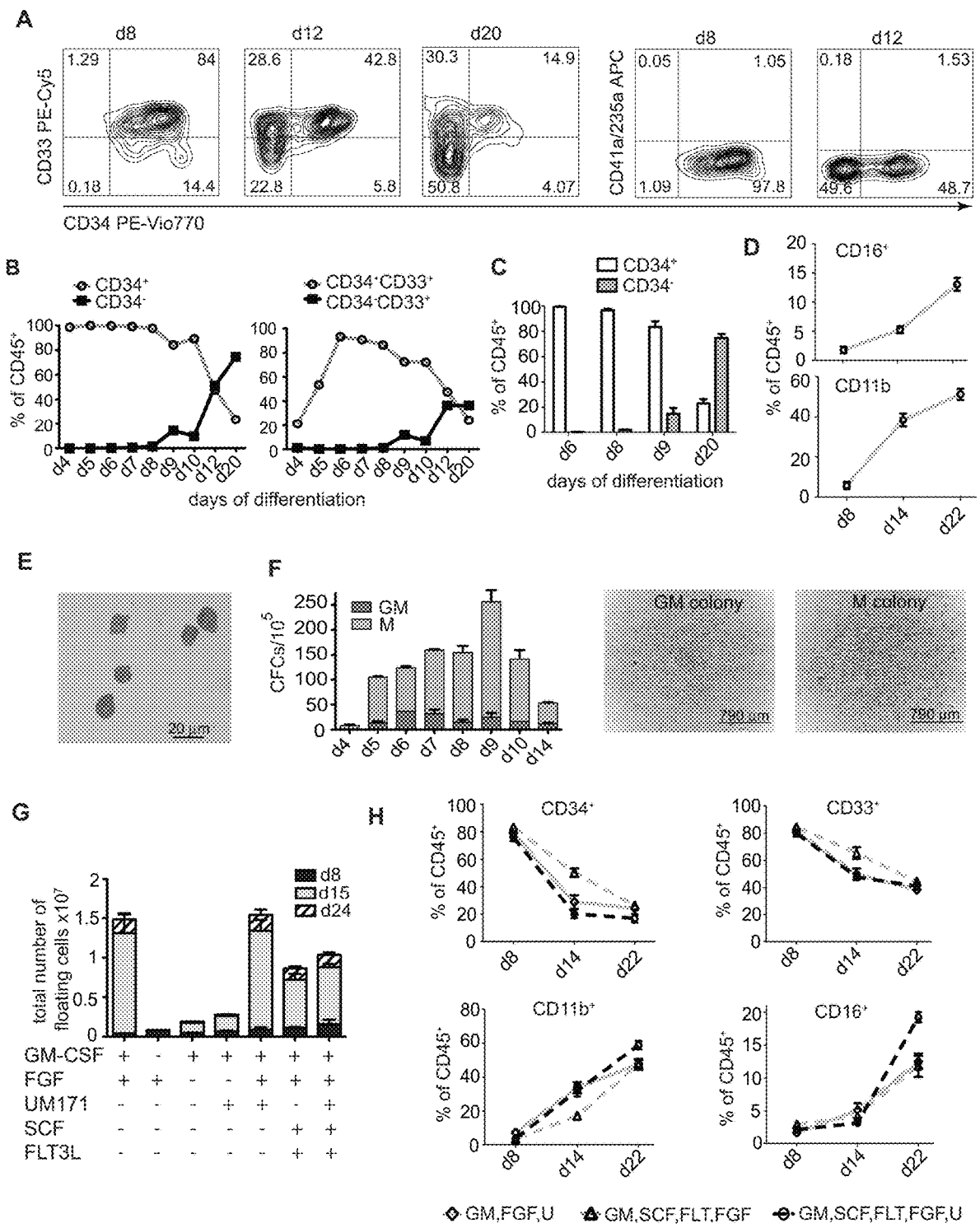
FIG. 2. Formation of myeloid progenitors in hiPSC cultures transduced with ETV2 mmRNA. (A) Flow cytometric analysis of CD34, CD33 and CD235a/CD41a expression in ETV2 mmRNA-transfected IISH2i-BM9 cultures differentiated in presence of GM-CSF and FGF2. (B) Representative experiment shows kinetics of CD34 and CD33 expression. (C) Bar graphs show proportion of CD34+ and CD34− cells in floating fraction at indicated days of differentiation. Results are mean+SE for 3 experiments. (D) Kinetics of CD11b and CD16 expression in cells collected from step 2 cultures. Error bars are +SE for 3 experiments. (E) Cytopsin showing the morphology of the myeloid progenitors generated in cultures after 10 days of differentiation. Scale bar is 20 μm. (F) Colony-forming potential of myeloid progenitors formed in cultures. Bars show mean±SE for 2 independent experiments performed in duplicates. Representative images of colonies formed by cells collected from step 2 cultures are shown. Scale bar is 790 μm. (G) Yield of floating cells from IISH2i-BM9 hiPSCs in presence of different cytokine combinations and UM171. Bars show mean±SE for 3 (GM-CSF, FGF, UM171) or 2 (remaining combinations) independent experiments. (H) Effect of different cytokine combinations on phenotype of myeloid cells. GM is GM-CSF, FGF is FGF2, FLT is FLT3L, U is UM171. Error bars are +SE for 3 experiments.

CD45+ cells generated in ETV2 mmRNA-induced cultures co-expressed CD34 and lacked expression of megakaryocytic and erythroid markers CD41 and CD235a (FIG. 2A). They quickly acquired early myeloid progenitor marker CD33 with more than 80% of total cells in suspension were positive for CD34 and CD33 on days 5-8 of differentiation (FIG. 2B-C). However, CD33 marker was gradually decreased while mature myeloid markers CD11b and CD16 gradually increased if floating cells are collected at later time points (FIG. 2D). Collected floating cells displayed myeloid progenitor morphology on cytospins (FIG. 2E) and possess GM- and M-CFC potential (FIG. 2F), thereby suggesting that the ETV2-induced program was mostly restricted to myelomonocytic cells. Kinetic analysis revealed that CFC potential of myeloid progenitors greatly increased from day 4 to day 9, but gradually decreased afterwards (FIG. 2F).

Next, we investigated the cytokine and growth factor requirements for optimal expansion of myeloid progenitors induced with ETV2. The presence of GM-CSF, which we identified as a the most critical factor for hPSC-derived myelomonocytic cells[8,18,19], was necessary for efficient production of myeloid progenitors as its removal substantially decreased the number of floating hematopoietic cells in cultures (FIG. 2G). Similarly, withdrawal of FGF2 reduced blood production in ETV2-induced cultures (FIG. 2G). To test whether myeloid cell production can be improved with the use of other cytokines or small molecules, we tested the effects of FLT3L, SCF and small molecule UM171, which has been shown to stimulate expansion of human cord blood CD34+ cells ex vivo[20] and iPSC-derived myeloid progenitors enriched in G-CFCs (Mesquitta et al. 2019). We have found that the presence of SCF and FLT3L slightly decreased the number of collected floating cells during differentiation, while UM171 had no significant effect on the number of hematopoietic cells. Flow cytometric analysis revealed no significant effect of studied cytokines and small molecule on myeloid cell phenotype in cultures (FIG. 2H). Thus, we concluded that FGF2 and GM-CSF are the two most critical cytokines to support myeloid lineage development in ETV2 mmRNA-transfected hiPSCs.

Induction of Neutrophils from ETV2-Induced Myeloid Progenitors

To induce formation of neutrophils from myeloid progenitors, we cultured them in StemSpan H3000 media with G-CSF and retinoic acid agonist Am580, which is known to promote neutrophil production from human somatic CD34+ cells[21]. After 7 days of culture in these conditions, we observed formation of cells with typical neutrophil phenotype and morphology (FIGS. 3A and 3B). Although myeloid progenitors produced some macrophages, they were adherent to the plate while the collected floating cells contained an population highly enriched in neutrophils (almost pure population) (FIG. 3B). Phenotypic analysis revealed that the majority of the collected floating cells expressed CD11b, MPO, and CD182, and greater than 50% were CD16-positive and expressed lactoferrin. However generated neutrophils expressed relatively low levels of CD66b and were lacking the CD10 marker which are typically present on mature peripheral blood neutrophils (FIG. 3A). Although the effect of UM171 on the output of myeloid progenitors in step 2 differentiation cultures was minimal, we noticed that cells from UM171-treated cultures generated much higher neutrophils in final differentiation step as compared to myeloid progenitors generated in cultures without UM171 (FIG. 3C). As mentioned previously, following collection of floating cells from step 2 differentiation cultures, adherent cells continued to generate myeloid progenitors that could be collected for an additional 2 weeks. Although the number of floating cells increased more than 10-fold following the second collection ($2^{nd}$ week; FIG. 1F), they produce fewer neutrophils as compared to myeloid progenitors collected at day 8 of differentiation (FIG. 3D). During the $3^{rd}$ week of culture, the number of collected floating myeloid cells dramatically decreased, although they were still able to differentiate into neutrophils. Overall, combining total neutrophil output from myeloid progenitor cultures collected over a three week period, we were able to generate up to $1.7 \times 10^7$ neutrophils from $10^6$ hiPSCs.

Functional Characterization Obtained from ETV2-Induced Myeloid Progenitors.

Figure 4:
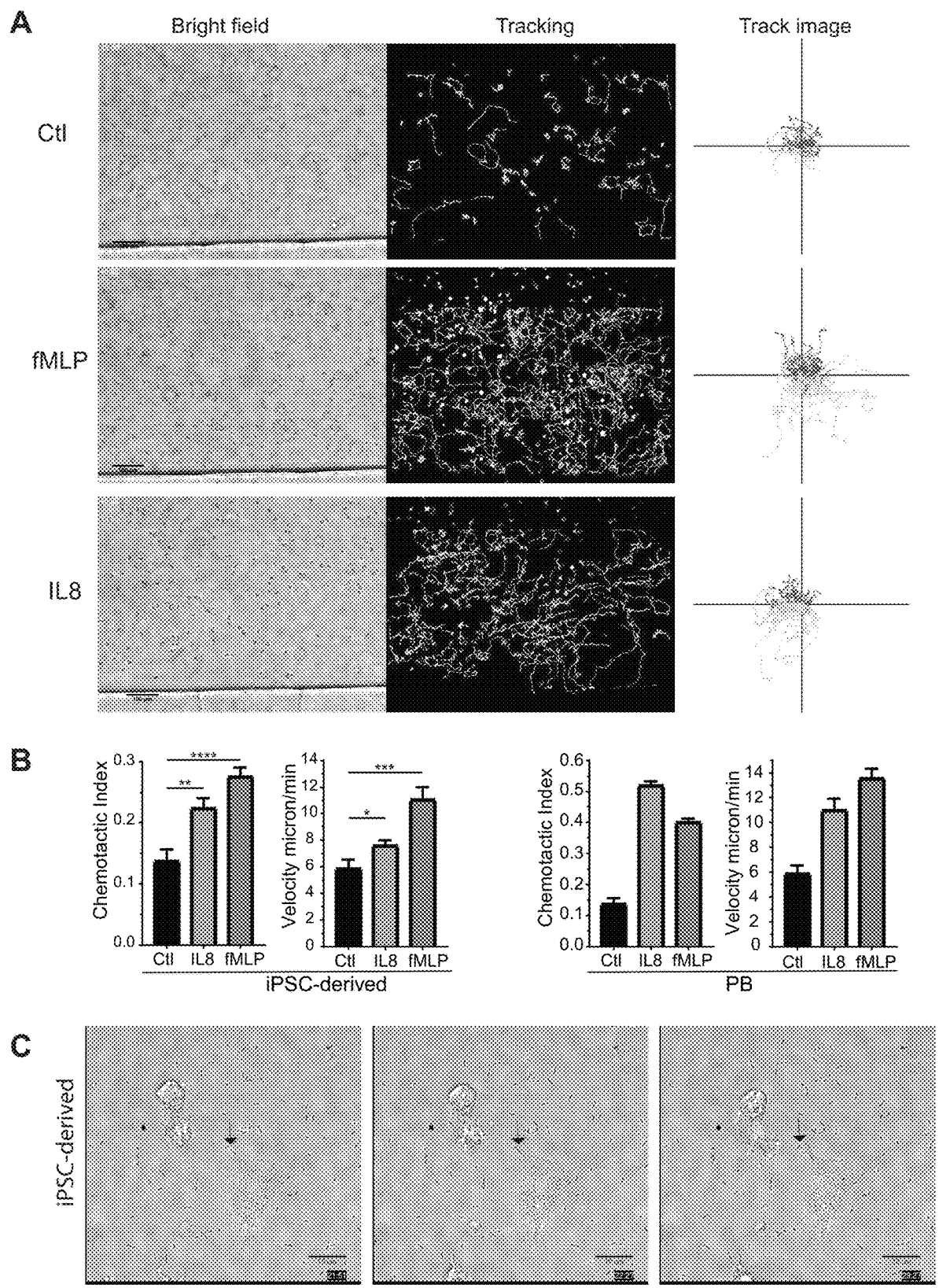
FIG. 4. Analysis of migratory potential of iPSC-derived neutrophils. (A) Images from 45 min time-lapse movies of hiPSC derived neutrophils during chemotaxis to vehicle control, fMLP or IL-8 on fibrinogen. Yellow lines showing automated cell tracking. Scale bar is 100 μm. (B) Quantification of chemotactic index and velocity of hiPSC neutrophils, showing significant differences of hiPSC neutrophils exposed to chemoattractant compared to treatment with vehicle control. P values for chemotactic index, control to IL8 $p=0.0040$, control to fMLP $p<0.0001$. P values for velocity, control to IL8 $p=0.0404$, control to fMLP $p=0.0009$ as determined by unpaired t test. Primary blood neutrophils showing chemotactic and velocity values. Bars show mean±SE from three independent experiments with technical replicates but not biological replicates for statistical analysis. (C) Montage image from high-resolution time-lapse movie of hiPSC neutrophils migrating and phagocytosing Pseudomonas aeruginosa. Arrow indicates one point during movie when cell is targeting bacteria. Scale bar is 10 μm. All functional assays with hiPSC-derived neutrophils were performed on batches obtained from myeloid progenitors collected at 8 or 12 days post-ETV2 transfection.
Figure 5:
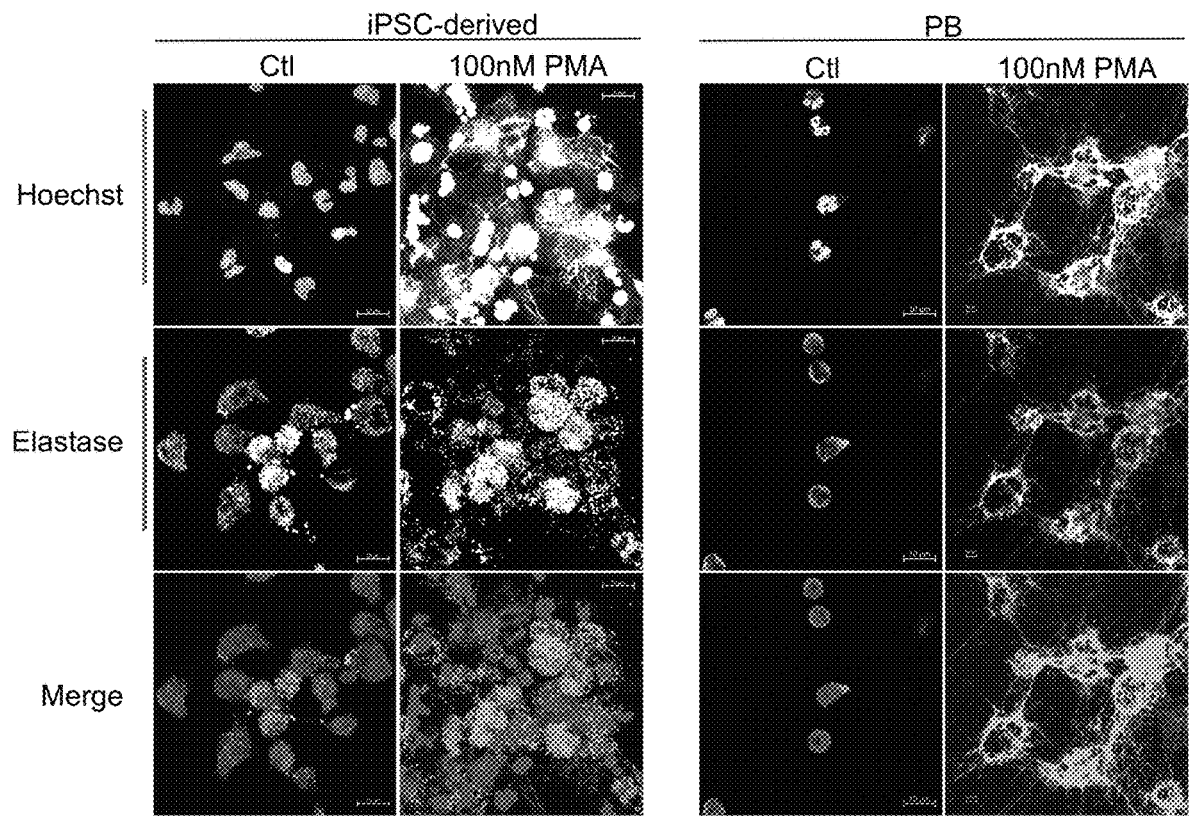
FIG. 5. Neutrophil extracellular trap (NET) formation. Maximum intensity projections of hiPSC and primary blood neutrophils. Both show characteristic multi lobed nuclei in blue and the azurophilic granule protein neutrophil elastase in green with control treatment. Upon treatment with 100 nM PMA both hiPSC and primary blood neutrophils form an extracellular fibril matrix composed of granule protein and chromatin, characteristic of NETs. Scale bar is 10 ᴁ m.

Functional analysis revealed that ETV2-induced neutrophils phagocytose pHrodo *E. coli* particles although we noticed the presence a population of immature myeloid progenitors lacking phagocytic activity in ex vivo generated cellular product (FIG. 3E). In addition, ETV2-induced neutrophils generated reactive oxygen species in response to treatment with phorbol esters (PMA) (FIG. 3F) and demonstrated chemotactic migration to fMLP and IL8 using microfluidic analysis (FIG. 4A-B). Although, the chemotactic index is not as robust as compared to primary human neutrophils (chemotactic index 0.4)[22], ETV2-derived neutrophils demonstrated directed migration to both IL8 and fMLP and improved chemotactic responses as compared to the neutrophil like PLB-985 cells[23]. Finally, the ETV2-induced neutrophils also chemotaxed to and phagocytosed the live bacteria *Pseudomonas aeruginosa* (FIG. 4C) and formed an extracellular fibril matrix composed of granule protein and chromatin, characteristic of NETs upon treatment with phorbol ester (100 nm PMA, FIG. 5). Taken together, these findings demonstrate that ETV2-induced neutrophils demonstrate phagocytic, chemotactic and signalling functions similar to primary human neutrophils.

Figure 8:
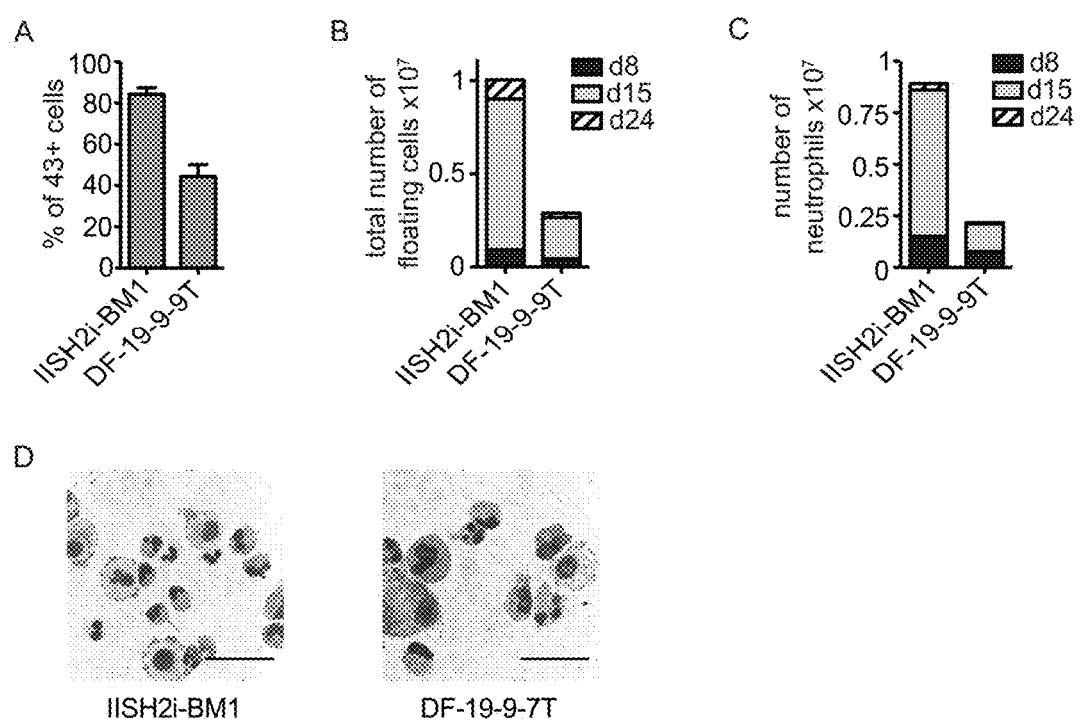
FIG. 8. Neutrophil production from IISH2i-BM9 and DF-19-7T iPSC lines using ETV2 modified mRNA. Proportion of CD43+ cells formed on day 8 of differentiation. (B) Total number of floating cells collected from differentiation cultures. (C) Total number of neutrophils produced in cultures. (D) Cytospins showing the morphology of the generated neutrophils.

Comparative Analysis of the Efficacy of the ETV2 mmRNA-Based Protocol for Neutrophil Induction from Different iPSC Lines Two more bone marrow-derived iPSC (IISH2i-BM1) and fibroblast-derived iPSC (DF-19-9-7T) lines were assessed for their capacity of inducing neutrophils differentiation using ETV2 mmRNA. Both cell lines were successfully programmed to myeloid progenitors, although with different efficiencies. Thus, for IISH1i-BM1 and DF-19-9-7T cell lines programming efficiency to CD43+ cells were 84% and 44%, respectively. After terminal differentiation step, neutrophils exhibited the expected morphology (FIG. 8).

Generation of Macrophages Using ETV2 Modified mRNA.

Figure 6:
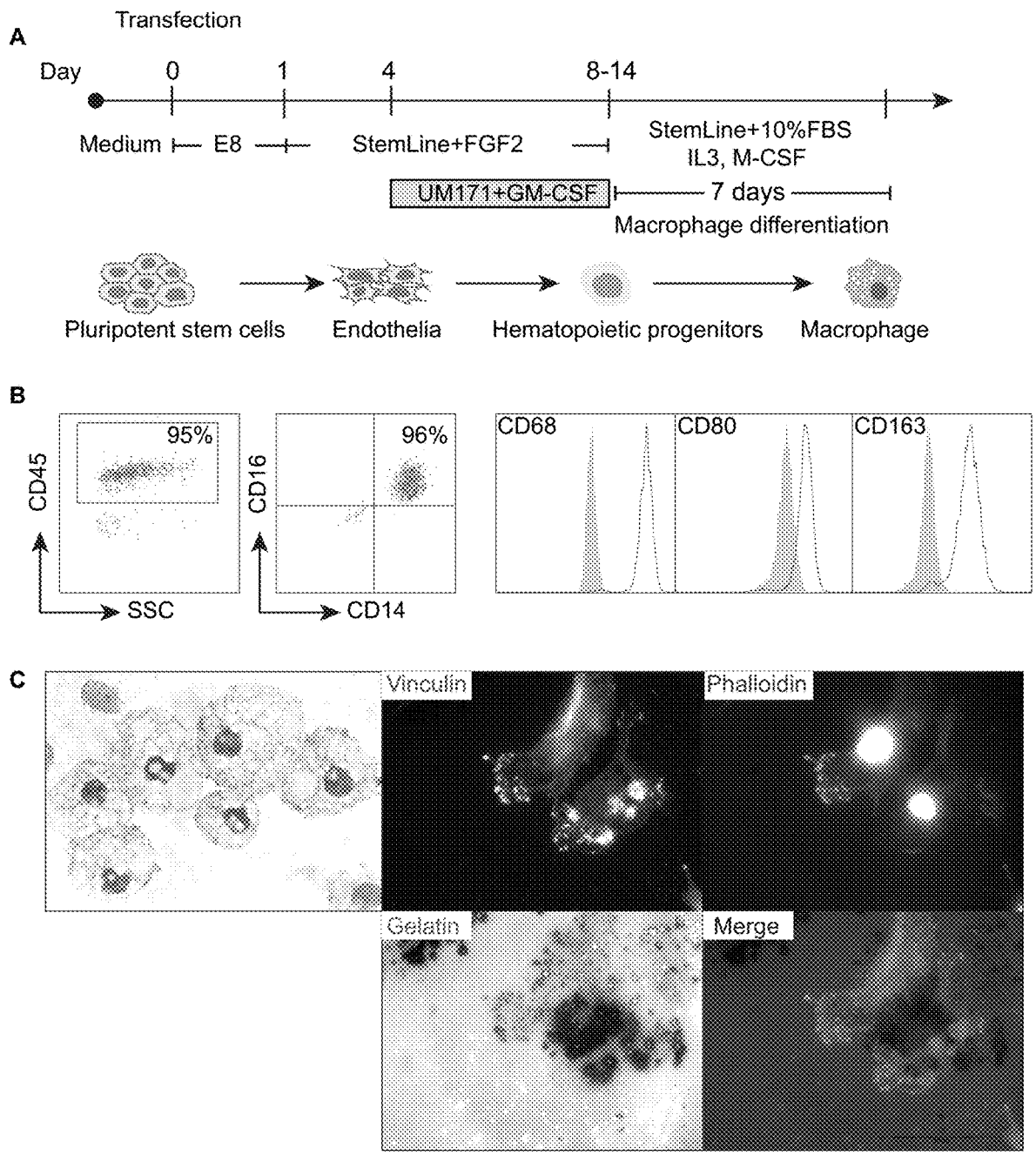
FIG. 6. Generation of macrophages using ETV2 modified mRNA. (A) Schematic diagram of protocol used for macrophage differentiation. (B) Phenotype of macrophages. (C) Macrophage morphology and podosome dynamics and matrix degradation.

Since ETV2 mmRNA-transfected cells generated large numbers of M-CFCs (FIG. 2F), we explored a potential of this approach for generation of macrophages. As shown in FIG. 6A-C, we found that culture of ETV2 cells with FGF2 and GM-CSF for 4 days, following culture with IL3 and M-CSF generated monocyte/macrophages with typical macrophage phenotype and morphology, which demonstrated invasive migration in gelatin.

DISCUSSION

In this Example, we developed a simple and efficient method for generating neutrophils from hiPSCs by triggering the myeloid hematoendothelial program with ETV2 mmRNA, subsequently inducing and expanding myeloid progenitors, and finally differentiating them into neutrophils. This method allows for neutrophil production in GMP-compatible conditions without feeder cells, serum and xenogenic components. The first batch of neutrophils can be obtained within a very short period of time (14 days after hiPSC transfection with ETV2 mmRNA). Because myeloid progenitors generated from ETV2 mmRNA-transfected cells continue generating neutrophil precursors for up to 3 weeks of culture in presence of GM-CSF, FGF2 and UM171, they can be collected weekly and used to produce neutrophils. This allows for total collection of up to $1.7 \times 10^7$ neutrophils from $10^6$ hiPSCs. Method described here is based on 2D culture system and is easily amendable to robotic manufacturing. Although neutrophils produced by this method had the capacity to produce reactive oxygen species, migrate in response to fMLP and IL8, phagocytose bacteria and form NETs, they were somewhat different from peripheral blood neutrophils and neutrophils produced from hPSCs in the presence of serum and feeders in our prior studies (Choi et al., 2009a). They had unique CD10-negative $CD66b^{low}$ phenotype and displayed somewhat reduced *E. coli* phagocytosis activity. CD10 is expressed in segmented neutrophils. However, CD10 expression is reduced in peripheral blood neutrophils from newborn infants or persons treated with G-CSF[24,25] while neutrophil activation with GM-CSF, TNF or complement component Sa increases CD10 expression[26,27]. Thus, it is possible that lack of CD10 expression may be associated with the unique serum-free conditions we are using for their differentiation. It has become clear that in addition to their phagocytic activities and the role in innate host defence, neutrophils contribute to the regulation of immune responses (reviewed in[28]). Further detailed analysis of function of hiPSC-derived neutrophils generated in our conditions will be essential to determine whether their unique phenotype is associated proinflammatory of immunosuppressive properties.

Successful generation of myeloid progenitors in our studies was achieved with ETV2 mmRNA. ETV2 belongs to the ETS family of transcription factors and is recognized as a master regulator of hematoendothelial fate, which is transiently expressed in specifying hematoendothelial progenitors[29-31]. ETV2 directly induces genes required for specification of hematopoietic and vascular cells including other ETS genes and GATA2 (reviewed in[31]). In our present studies, we revealed that transient transfection hiPSCs with ETV2 is sufficient to induce hematoendothelial progenitors that can be subsequently differentiated to neutrophils. Compared to classical differentiation methods, direct ETV2-mediated programming proceeds without transition through the mesodermal stage and requires a minimal numbers of growth factors (FGF2, GM-CFC and G-CSF) to achieve neutrophil differentiation, thereby allowing for cost-efficient production of neutrophils. Overall, this innovative neutrophil differentiation protocol appears to be useful for generating neutrophils for potential blood transfusion and gene-therapies based on terminally differentiated cells. These cells, unlike primary human neutrophils, are amenable to genetic manipulation.

This method can be adopted to a bioreactor platform to enable clinical translation.

In addition, we demonstrated that ETV2 mmRNA-based protocol can be used to generate macrophages.

Materials and Methods.

Cell Culture

Bone marrow-derived iPSC (IISH2i-BM9 and IISH2i-BM1)[32], were obtained from WiCell (Madison, Wis.). Peripheral blood iPSC was earlier derived by our group ( ). iPSCs were cultured on Matrigel-coated tissue culture plates in E8 medium (Stem Cell Technologies).

mmRNA Synthesis and Transfection

Human ETV2 transcript variant 1(NM_014209.3) was cloned into 5'-MCS-1B construct as previously described[17]. To generate IVT templates with a 180-A tract, a reverse primer containing 180 T base pairs and ATCGGTGCGGGCCTCTTCGCTA (SEQ ID NO:10) forward primer including T7 promoter were used in a PCR reaction. All PCR reactions were carried out using Phusion (Thermo Fisher Scientific). The mmRNA was synthesized using the MEGAscript T7 kit (Ambion, Austin, Tex.), using a custom ribonucleoside cocktail comprised of 3'-0-Me-m7G(5')ppp(5')G ARCA cap analog, pseudouridine triphosphate (TriLink Biotechnologies, San Diego, Calif.), adenosine triphosphate, guanosine triphosphate and cytidine triphosphate. The synthesis reactions were setup according to the manufacturer's instructions. Reactions were incubated 3 hours at 37° C. and treated with DNAse. RNA was purified using PureLink RNA Mini kit (Thermo Fisher Scientific) and adjusted with RNase-free water to 100 ng/µl working concentration before being stored at −80° C. Undifferentiated hiPSCs were transfected with using TransIT-mRNA reagent in E8 media containing ROCK inhibitor[17], or by electroporation[13]. Briefly, for transfection, single cell suspension was prepared using HyQtase (Thermo Fisher Scientific). Per one well of transfection, a total of $2 \times 10^5$ cells in 1 ml complete E8 medium with 10 µM ROCK inhibitor (StemCell Technologies, Vancouver, Canada) were plated into a collagen IV-coated 6-well plate. 30-60 minutes later, a mixture of 200 ng ETV2:TransIT-mRNA (Mirus Bio, Madison, WI) was added to each well according to the manufacturer's instructions. For electroporation, $10^6$ cells were nucleofected with 800 ng of mmETV2 in 100 µl of nucleofection buffer (Amaxa Human Stem Cell Nucleofector® Kit 2; Lonza), using Amaxa Nucleofector II B-016 program. After nucleofection, cells were divided equally between 4 wells of collagen IV-coated 6-well plate.

Feeder-Free Xeno- and Serum-Free Generation of Neutrophils from hiPSC.

The following day after transfection (day 1), media was changed with 1 ml of StemLine II (Sigma) supplemented with 20 ng/ml of human FGF2 (Peprotech). On day two, 1 ml of the same media was added. On day 3, media was changed and 1 ml of StemLineII supplemented with FGF2 (20 ng/ml), GM-CSF (25 ng/ml) (Peprotech) and UM171 (50 nM; Xcess Biosciences, Inc.) This media was added daily up to day 8/12. On day 8/12, floating cells were gently harvested and used for terminal neutrophil differentiation. Following the first collection of floating cells, 2 ml of StemLineII supplemented with FGF2, GM-CSF, and UM171 was added to the remaining adherent cells. Additional 2 ml of the same media was added every two days until the next round of floating cell collection on days 16/19. Similar procedure was followed for $3^{rd}$ round of cell collection on 23/29 days. To induce neutrophil terminal differentiation, floating cells were cultured in StemSpanH300 media (Stem Cell Technologies), supplemented with Glutamax 100× (Thermo), ExCyte 0.2% (Merck Millipore), human G-CSF (150 ng/ml; Amgen) and Am580 retinoic acid agonist 2.5 μM (Sigma Aldrich), Gentamycin (1000×) (Life Technologies) at $5\times10^5$ cells/ml density. After 4 days, 2 ml of the same media with all components and cytokines were added on the top of existing culture. Mature neutrophils were gently harvested after 6-8 days of culture from supernatant, leaving the adherent macrophages, and filtered through a 70 μM mesh (Falcon, Life Sciences) before analysis.

Flow Cytometry

To analyse cell surface markers, $5\times10^5$ cells were stained in FACS buffer with appropriate antibodies (Table 1). Ghost Dye™ (Tonbo Biosciences, San Diego, CA) was used to analyse the live cell population. For intracellular staining cells were resuspended in Fixation Reagent (Medium A) (Invitrogen™) and incubated at room temperature for 15 minutes. After washing cells with PBS, cells were resuspended in 100 μl of Permeabilization Reagent (Medium B) (Invitrogen™) and stained with Lactoferrin or MPO antibody (Table 1) for 15 minutes. Cells were analysed by using MACSQuant Analyzer 10 (Miltenyi Biotec Inc, San Diego, CA) or ThermoFisher Attune and FlowJo software (Tree Star, Ashland, OR).

TABLE 1

Antibodies used in this study.

| Antigen | Conjugate | Source | Cat No. |
| --- | --- | --- | --- |
| CD10 | BV510 | BD Biosciences | 563032 |
| CD11b | APC | BD Biosciences | 550019 |
| CD11b | PE | Life Technologies | 12-0118-42 |
| CD15 | BV711 | BD Biosciences | 563142 |
| CD16 | FITC | Life Technologies | 11-0168-42 |
| CD16 | APC | Life technologies | 17-0168-42 |
| CD16 | PE-Cy7 | BD Biosciences | 557744 |
| CD33 | PE-Cy5 | Biolegend | 303406 |
| CD34 | PE-Vio770 | Miltenyi Biotec | 130-100-844 |
| CD34 | FITC | BD Biosceinces | 555821 |
| CD41a | APC | BD Biosceinces | 559777 |
| CD43 | VioBlue | Miltenyi Biotec | 130-097-373 |
| CD45 | PE | Miltenyi Biotec | 130-113-118 |
| CD45 | PE-Vio770 | Miltenyi Biotec | 130-110-634 |
| CD45 | APC-Vio770 | Miltenyi Biotec | 130-110-773 |
| CD66b | PE | BD Biosciences | 561650 |
| CD144 | PE-Vio770 | Miltenyi Biotec | 130-100-720 |
| CD182 | PE | Invitrogen | 12-1829-42 |
| CD235a | APC | BD Biosceinces | 551336 |
| Lactoferrin | PE | Life Technologies | GIC206 |
| MPO | FITC | Invitrogen | 11-1299-42 |
| Ghost red | 780 | Tonbo Biosciences | 13-0865-T100 |

Wright-Giemsa Staining

To assess the morphology of cells within colonies, cells were fixed on glass slides using a Cytospin centrifuge (Cytospin 2; Thermo Shandon Inc.), stained with Wright-Giemsa solution (Sigma-Aldrich), and then observed under a light microscope (Olympus).

Colony-Forming Cell Assay

Total cells were collected daily from day 4 to 10 and floating cells from day 14 cultures were subjected to hematopoietic clonogenic assay. Colony assays were performed using serum-containing MethoCult 4435 (StemCell Technologies, Vancouver, BC, Canada) in 35-mm low-adherent culture dishes (StemCell Technologies) according to the manufacture's protocol. Colony types were evaluated after 14 days of incubation at 37° C., 5% $CO_2$ by inverted light microscopy (Olympus, Tokyo).

Chemotaxis Assay

Chemotaxis was assessed using a microfluidic device as described previously (Yamahashi et al., 2015). In brief, PDMS devices were plasma treated and adhered to glass coverslips. Devices were coated with 10 ng/mL fibrinogen (Sigma) in PBS for 30 min at 37° C., 5% CO2. The devices were blocked with 2% BSA-PBS for 30 min at 37° C., 5% CO2 to block non-specific binding and then washed twice with mHBSS. Cells were stained with calcein AM (Molecular Probes) in PBS for 10 min at room temperature followed by resuspension in mHBSS. Cells were seeded at $5\times10^6$/mL to allow adherence for 30 min before addition of chemoattractant. Either 1 μM fMLP (Sigma) or 11.25 μM IL8 (R&D Systems) was loaded into the devices. Cells were imaged for 45-90 min every 30 sec on a Nikon Eclipse TE300 inverted fluorescent microscope with a 10× objective and an automated stage using Metamorph software (Molecular Devices). Automated cell tracking analysis was done using JEX software (Warrick et al., 2016) to calculate chemotactic index and velocity.

Phagocytosis

Phagocytosis was assessed using pHrodo™ Green E. coli Bioparticles™ Conjugate (Invitrogen™) according to a modified manufacturer's protocol. pHrodo™ Green E. coli beads were resuspended in 2 ml of PBS and sonicated with an ultrasonicator 3 times (20% amplitude, 20s on/10s off). 100nl beads per assay were opsonized by mixing with opsonizing reagent at a 1:1 ratio and incubated at 37° C. for 1 hour. Beads were washed 3 times mHBSS buffer by centrifugation at 4° C., 1500 RCF for 15 minutes then final resuspension in mHBSS buffer. Beads were used immediately or stored at 4° C. for several days. $5\times10^5$ cells were resuspended in 100 μl of opsonized bead solution and incubated at 37° C. or on ice for 1 hour. Phagocytosis was stopped by placing all samples on ice. Analysis was carried out with ThermoFisher Attune cytometer for fluorescent particles (509/533). Cells were gated based on granulocyte population, single cells and live cells using propidium iodine.

Phagocytosis Imaging

Overnight culture of Pseudomonas aeruginosa was diluted 1:4 and grown in LB at 37° C. for about 2 hours, or until a 1:100 dilution, $O.D._{600}$ of 0.3 was reached. Empirically determined, cells were diluted to 1000 cfu's/nl, in our hands $O.D._{600}$ 2.5. $2^5$ hiPSC-derived neutrophils were mixed with $2^6$ bacteria in mHBSS then plated on glass coverslip coated with 10 μg/ml fibrinogen and imaged at 37c on a Nikon Eclipse TE300 inverted fluorescent microscope with a 60× oil immersion objective and an automated stage using Metamorph software.

Measurement of ROS Production in Neutrophils.

$10^5$ floating cells were plated in each well of a black 96 well plate on 10 μg/ml fibrinogen with 100 μl of mHBSS buffer in the presence of 10 ng/ml Dihydrorhodamine 123.

Cells were incubated for 30 min at 37° C./5% CO2. PMA was added to final concentration of 50 ng/ml or vehicle control DMSO was added to samples. Optimal reactive oxygen species production was determined by time course. Fluorescent measurements were taken of samples in triplicate or replicates of four on the Victor$^3$ V plate reader (Ex/Em 500/536).

Neutrophil Extracellular Traps (NETs) Formation $2^5$ hiPSC or primary blood neutrophils were plated on 12 mm glass coverslips coated with 10 µg/ml fibrinogen and blocked with 2% BSA. Cells were allowed to adhere for 30 min then treated, or not with 100 nM PMA for four hours. Assay was stopped with fixation by gentle addition of paraformaldehyde to 4% final concentration for 15 min. Cells were stained with human neutrophil Elastase for 1 hour in 5% goat serum then stained with Hoechst 33342 for 10 minutes before mounting. Cells were imaged with LSM 800 Zeiss Airyscan 60× oil emersion lens.

Statistical Analysis

All the data were obtained from 2-3 independent experiments and reported as mean±SD or ±SEM. All the graphs and statistics were performed using GraphPad Prism software (GraphPad, San Diego, CA).

REFERENCES

1. Lyman, G. H. & Poniewierski, M. S. A Patient Risk Model of Chemotherapy-Induced Febrile Neutropenia: Lessons Learned From the ANC Study Group. *J Natl Compr Canc Netw* 15, 1543-1550 (2017).
2. Castagnola, E. et al. A prospective study on the epidemiology of febrile episodes during chemotherapy-induced neutropenia in children with cancer or after hemopoietic stem cell transplantation. *Clin Infect Dis* 45, 1296-1304 (2007).
3. Graw, R. G., Jr., Herzig, G., Perry, S. & Henderson, E. S. Normal granulocyte transfusion therapy: treatment of septicemia due to gram-negative bacteria. *N Engl J Med* 287, 367-371 (1972).
4. Valentini, C. G., Farina, F., Pagano, L. & Teofili, L. Granulocyte Transfusions: A Critical Reappraisal. *Biol Blood Marrow Transplant* 23, 2034-2041 (2017).
5. Gurlek Gokcebay, D. & Akpinar Tekgunduz, S. Granulocyte transfusions in the management of neutropenic fever: A pediatric perspective. *Transfus Apher Sci* 57, 16-19 (2018).
6. Gea-Banacloche, J. Granulocyte transfusions: A concise review for practitioners. *Cytotherapy* 19, 1256-1269 (2017).
7. West, K. A., Gea-Banacloche, J., Stroncek, D. & Kadri, S. S. Granulocyte transfusions in the management of invasive fungal infections. *Br J Haematol* 177, 357-374 (2017).
8. Choi, K. D., Vodyanik, M. A. & Slukvin, II Generation of mature human myelomonocytic cells through expansion and differentiation of pluripotent stem cell-derived lin-CD34+CD43+CD45+ progenitors. *J Clin Invest* 119, 2818-2829 (2009).
9. Lachmann, N. et al. Large-scale hematopoietic differentiation of human induced pluripotent stem cells provides granulocytes or macrophages for cell replacement therapies. *Stem cell reports* 4, 282-296 (2015).
10. Saeki, K. et al. A feeder-free and efficient production of functional neutrophils from human embryonic stem cells. *Stem Cells* 27, 59-67 (2009).
11. Sweeney, C. L. et al. Molecular Analysis of Neutrophil Differentiation from Human Induced Pluripotent Stem Cells Delineates the Kinetics of Key Regulators of Hematopoiesis. *Stem Cells* 34, 1513-1526 (2016).
12. Trump, L. R. et al. Neutrophils Derived from Genetically Modified Human Induced Pluripotent Stem Cells Circulate and Phagocytose Bacteria In Vivo. *Stem Cells Transl Med* (2019).
13. Elcheva, I. et al. Direct induction of haematoendothelial programs in human pluripotent stem cells by transcriptional regulators. *Nat Commun* 5, 4372 (2014).
14. Kang, H. et al. GATA2 Is Dispensable for Specification of Hemogenic Endothelium but Promotes Endothelial-to-Hematopoietic Transition. *Stem cell reports* (2018).
15. Zhao, H. & Choi, K. A CRISPR screen identifies genes controlling Etv2 threshold expression in murine hemangiogenic fate commitment. *Nat Commun* 8, 541 (2017).
16. Hayashi, M. et al. Endothelialization and altered hematopoiesis by persistent Etv2 expression in mice. *Exp Hematol* 40, 738-750 e711 (2012).
17. Suknuntha, K. et al. Optimization of Synthetic mRNA for Highly Efficient Translation and its Application in the Generation of Endothelial and Hematopoietic Cells from Human and Primate Pluripotent Stem Cells. *Stem Cell Rev* 14, 525-534 (2018).
18. Choi, K. D. et al. Hematopoietic and endothelial differentiation of human induced pluripotent stem cells. *Stem Cells* 27, 559-567 (2009).
19. Slukvin, L I., Vodyanik, M. A., Thomson, J A., Gumenyuk, M. E. & Choi, K. D. Directed differentiation of human embryonic stem cells into functional dendritic cells through the myeloid pathway. *Journal of Immunology* 176, 2924-2932 (2006).
20. Fares, I. et al. Cord blood expansion. Pyrimidoindole derivatives are agonists of human hematopoietic stem cell self-renewal. *Science* 345, 1509-1512 (2014).
21. Li, L. et al. Am80-GCSF synergizes myeloid expansion and differentiation to generate functional neutrophils that reduce neutropenia-associated infection and mortality. *EMBO Mol Med* 8, 1340-1359 (2016).
22. Powell, D. et al. Chemokine Signaling and the Regulation of Bidirectional Leukocyte Migration in Interstitial Tissues. *Cell Rep* 19, 1572-1585 (2017).
23. Cavnar, P. J., Mogen, K., Berthier, E., Beebe, D. J. & Huttenlocher, A. The actin regulatory protein HS1 interacts with Arp2/3 and mediates efficient neutrophil chemotaxis. *J Biol Chem* 287, 25466-25477 (2012).
24. Penchansky, L., Pirrotta, V. & Kaplan, S. S. Flow cytometric study of the expression of neutral endopeptidase (CD10/CALLA) on the surface of newborn granulocytes. *Mod Pathol* 6, 414-418 (1993).
25. Zarco, M. A. et al. Phenotypic changes in neutrophil granulocytes of healthy donors after G-CSF administration. *Haematologica* 84, 874-878 (1999).
26. Kuijpers, T. W. et al. Membrane surface antigen expression on neutrophils: a reappraisal of the use of surface markers for neutrophil activation. *Blood* 78, 1105-1111 (1991).
27. Werfel, T., Sonntag, G., Weber, M. H. & Gotze, O. Rapid increases in the membrane expression of neutral endopeptidase (CD10), aminopeptidase N (CD13), tyrosine phosphatase (CD45), and Fc gamma-RIII (CD16) upon stimulation of human peripheral leukocytes with human C5a. *J Immunol* 147, 3909-3914 (1991).
28. Scapini, P., Marini, O., Tecchio, C. & Cassatella, M. A. Human neutrophils in the saga of cellular heterogeneity: insights and open questions. *Immunol Rev* 273, 48-60 (2016).

29. Kataoka, H. et al. Etv2/ER71 induces vascular mesoderm from Flk1+PDGFRalpha+ primitive mesoderm. *Blood* 118, 6975-6986 (2011).
30. Garry, D. J. Etv2 IS A MASTER REGULATOR OF HEMATOENDOTHELIAL LINEAGES. *Trans Am Clin Climatol Assoc* 127, 212-223 (2016).
31. Sumanas, S. & Choi, K. ETS Transcription Factor ETV2/ER71/Etsrp in Hematopoietic and Vascular Development. *Curr Top Dev Biol* 118, 77-111 (2016).
32. Hu, K. et al. Efficient generation of transgene-free induced pluripotent stem cells from normal and neoplastic bone marrow and cord blood mononuclear cells. *Blood* 117, e109-119 (2011).
33. Yamahashi, Y. et al. Integrin associated proteins differentially regulate neutrophil polarity and directed migration in 2D and 3D. *Biomed Microdevices* 17, 100 (2015).
34. Warrick, J. W., Timm, A., Swick, A. & Yin, J. Tools for Single-Cell Kinetic Analysis of Virus-Host Interactions. *PLoS One* 11, e0145081 (2016).
35. Ackermann M, Kempf H, Hetzel M, et al. Bioreactor-based mass production of human iPSC-derived macrophages enables immunotherapies against bacterial airway infections. *Nat Commun.* 2018; 9(1):5088, Published 2018 Nov. 30, doi:10.1038/s41467-018-07570-7.

Each publication, patent, and patent publication cited in this disclosure is incorporated by reference herein in its entirety. The present invention is not intended to be limited to the foregoing examples, but encompasses all such modifications and variations as come within the scope of the appended claims.

We claim:

1. A population of in vitro derived CD 16+ CD 10− neutrophils obtained by an in vitro method of producing CD 16+ CD 10− neutrophils from pluripotent stem cells (PSCs), the method comprising:
   (a) introducing exogenous ETS Variant Transcription Factor 2 (ETV2) in the PSCs and culturing the ETV2-induced PSCs in, xenogen- and serum-free medium comprising fibroblast growth factor receptor 2 (FGF-2) to produce a population of ETV2-induced CD144+ hematoendothelial progenitor cells (ETV2-induced HEPs);
   (b) culturing the ETV2-induced CD 144+hematoendothelial progenitor cells in xenogen- and serum-free medium comprising granulocyte-macrophage colony-stimulating factor (GM-CSF) and FGF-2 for a sufficient time to produce non-adherent myeloid progenitors; and
   (c) culturing the myeloid progenitors in xenogen- and serum-free medium comprising G-CSF and retinoic acid agonist to differentiate the non-adherent myeloid progenitors into CD16+ CD10− neutrophils,
   wherein the CD16+ CD10− neutrophils exhibit impaired neutrophil extracellular trap (NET) production in response to phorbol 12-myristate 13-acetate (PMA),
   wherein the neutrophils have a CD66b$^{low}$ phenotype,
   wherein greater than 50% of the neutrophils are CD 16+, and
   wherein the pluripotent stem cell is genetically modified to obtain the neutrophil population of interest.

2. The population of claim 1, wherein the CD 16+ CD 10− neutrophils express one or more of the neutrophil markers CD15, CD66b, CD182, myeloperoxidase (MPO) and lactoferrin, and display neutrophil morphology.

3. The population of claim 1, wherein the exogenous ETV2 is introduced transiently.

4. The population of claim 1, wherein the exogenous ETV2 is introduced via an episomal vector.

5. The population of claim 1, wherein the exogenous ETV2 is transposon expression vector.

6. The population of claim 1, wherein the exogenous ETV2 is integrated into the PSCs.

* * * * *